(12) United States Patent
Michihata et al.

(10) Patent No.: US 10,893,247 B2
(45) Date of Patent: Jan. 12, 2021

(54) MEDICAL SIGNAL PROCESSING DEVICE AND MEDICAL OBSERVATION SYSTEM

(71) Applicant: Sony Olympus Medical Solutions Inc., Tokyo (JP)

(72) Inventors: Taihei Michihata, Kanagawa (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 19 days.

(21) Appl. No.: 15/893,832

(22) Filed: Feb. 12, 2018

(65) Prior Publication Data
US 2018/0249139 A1 Aug. 30, 2018

(30) Foreign Application Priority Data
Feb. 24, 2017 (JP) ................. 2017-033936

(51) Int. Cl.
| | | |
|---|---|---|
| H04N 9/69 | (2006.01) | |
| G06T 7/13 | (2017.01) | |
| H04N 5/232 | (2006.01) | |
| A61B 1/00 | (2006.01) | |
| A61B 1/04 | (2006.01) | |
| G06T 5/00 | (2006.01) | |
| A61B 1/045 | (2006.01) | |
| G06T 5/40 | (2006.01) | |
| A61B 1/06 | (2006.01) | |
| A61B 1/07 | (2006.01) | |

(52) U.S. Cl.
CPC .......... *H04N 9/69* (2013.01); *A61B 1/00006* (2013.01); *A61B 1/00009* (2013.01); *A61B 1/00045* (2013.01); *A61B 1/00101* (2013.01); *A61B 1/00105* (2013.01); *A61B 1/00186* (2013.01); *A61B 1/00188* (2013.01); *A61B 1/042* (2013.01); *A61B 1/045* (2013.01); *G06T 5/009* (2013.01); *G06T 5/40* (2013.01); *G06T 7/13* (2017.01); *H04N 5/23229* (2013.01); *A61B 1/00117* (2013.01); *A61B 1/0669* (2013.01); *A61B 1/07* (2013.01); *G06T 2207/10024* (2013.01); *G06T 2207/10068* (2013.01)

(58) Field of Classification Search
CPC    H04N 5/202; H04N 9/73; H04N 9/69; G09G 3/3406
See application file for complete search history.

(56) References Cited

U.S. PATENT DOCUMENTS

| | | | | |
|---|---|---|---|---|
| 2005/0179821 A1* | 8/2005 | Suga | ........................ | H04N 5/20 348/687 |
| 2006/0077490 A1* | 4/2006 | Sheraizin | .................. | G06T 5/40 358/519 |
| 2007/0092154 A1* | 4/2007 | Kato | .................. | H04N 5/23245 382/254 |
| 2008/0079735 A1* | 4/2008 | Selwan | ................ | G09G 3/3611 345/505 |

FOREIGN PATENT DOCUMENTS

JP         2014-12037         1/2014

* cited by examiner

*Primary Examiner* — Clifford Hilaire
(74) *Attorney, Agent, or Firm* — Xsensus LLP

(57) ABSTRACT

A medical signal processing device for processing an image obtained by an imaging unit including a plurality of pixels, and generating a video signal for display, includes a Y gamma-correction unit that performs Y gamma-correction on a luminance signal for each pixel in the image obtained by the imaging unit.

7 Claims, 19 Drawing Sheets

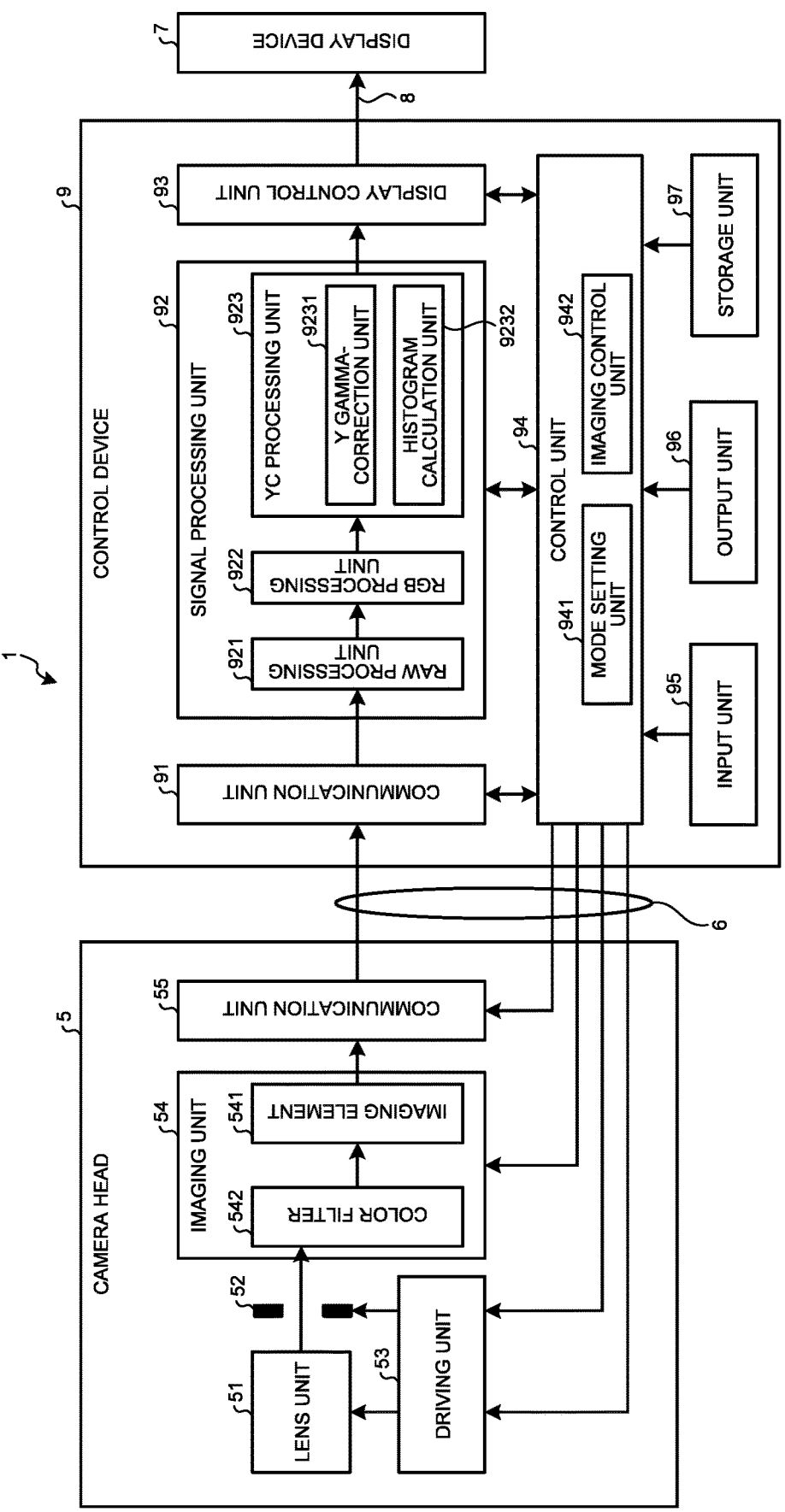

FIG.11
(a)
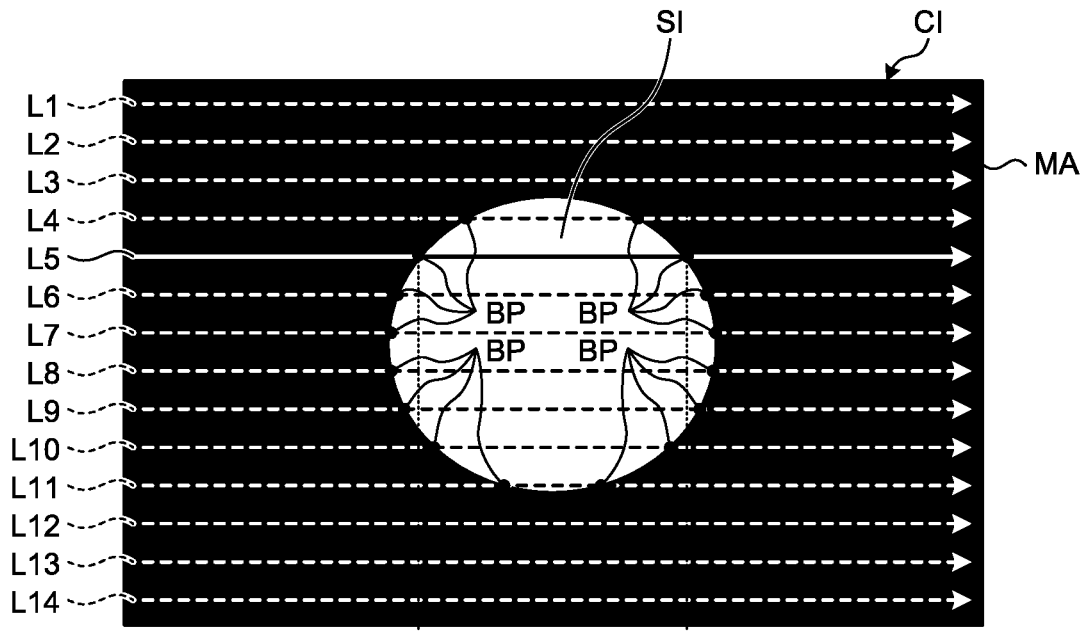
(b)
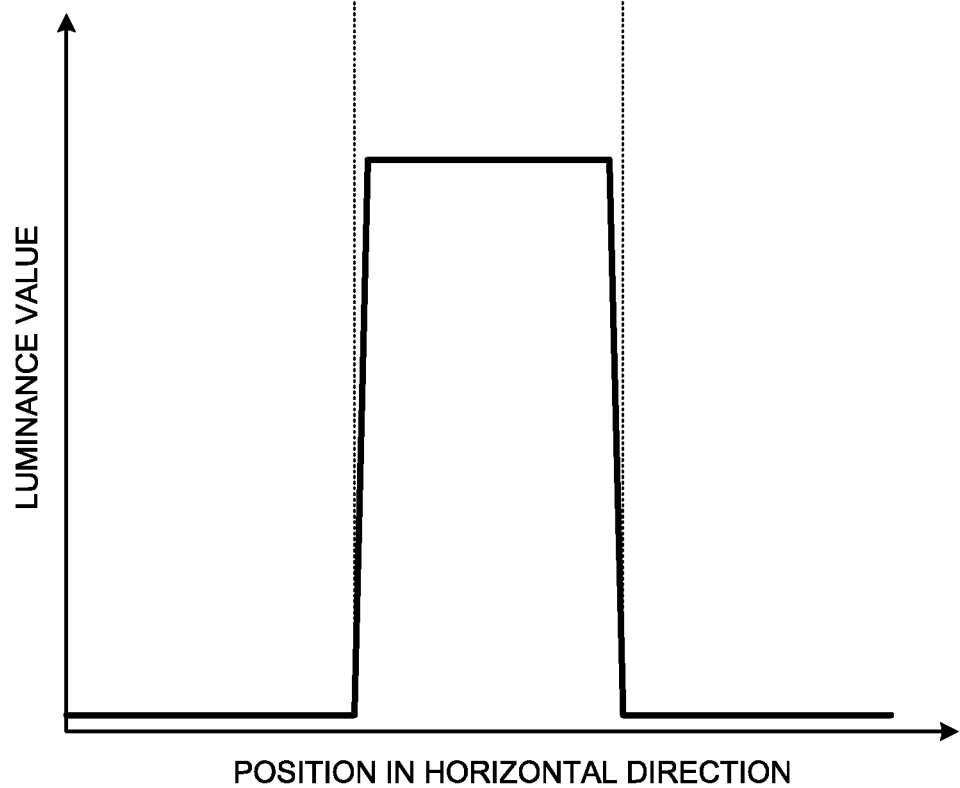

MEDICAL SIGNAL PROCESSING DEVICE AND MEDICAL OBSERVATION SYSTEM

CROSS-REFERENCE TO RELATED APPLICATION

The present application claims priority to and incorporates by reference the entire contents of Japanese Patent Application No. 2017-033936 filed in Japan on Feb. 24, 2017.

BACKGROUND

The present disclosure relates to a medical signal processing device for generating a video signal for display by processing an image obtained by an imaging unit including a plurality of pixels, and also to a medical observation system including such a medical signal processing device.

In the medical fields, medical observation systems for imaging the inside of a subject such as a person (the inside of a living body) and observing the inside of the living body have been known (for example, see Japanese Patent Application Laid-open No. 2014-12037).

The medical observation system (endoscopic device) according to Japanese Laid-open Patent Publication No. 2014-12037 includes: an insertion unit that is inserted into a living body, images the inside of the living body, and outputs an image signal; a main body unit that processes the image signal and generates a video signal for display; and a display unit that displays an endoscopic image based on the video signal.

SUMMARY

In some endoscopic images, a bright part may result in white, a dark part may result in black, or a forceps or white gauze may get in the images of a subject to make the images appear brighter as a whole. In those cases, doctors and other medical staff fail to observe the part that they want to observe in fact. That is to say, an endoscopic image suitable for observation may not be displayed and the convenience may not be improved.

In order to solve such problems, a plurality of imaging elements with different sensitivities are used. Using the imaging elements, however, makes the structure complicated.

A medical signal processing device according to one aspect of the present disclosure processes an image obtained by an imaging unit including a plurality of pixels, generates a video signal for display, and includes a Y gamma-correction unit that performs Y gamma-correction on a luminance signal for each pixel in the image obtained by the imaging unit.

BRIEF DESCRIPTION OF THE DRAWINGS

FIG. 2 is a block diagram illustrating a structure of a camera head and a control device;

FIG. 11 is a diagram for describing a mask edge detection process;

DETAILED DESCRIPTION

Figure 1:
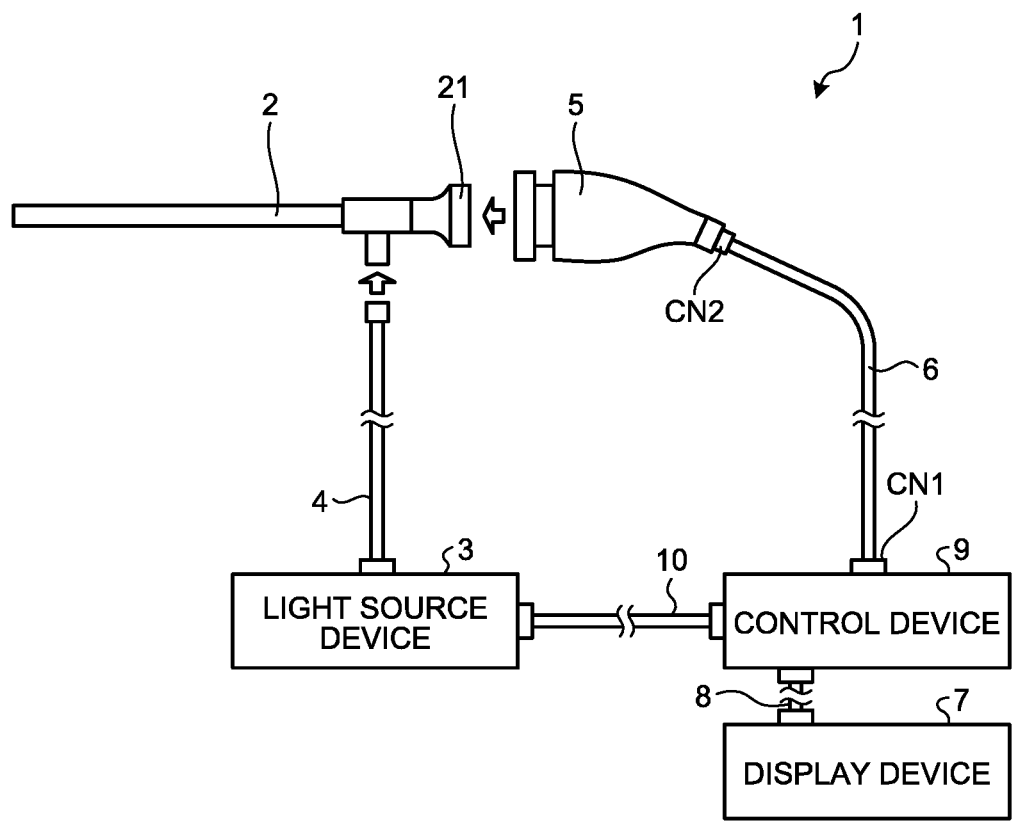
FIG. 1 is a diagram illustrating a schematic structure of a medical observation system according to a first embodiment.

Embodiments for carrying out the present disclosure (hereinafter, embodiments) will hereinafter be described with reference to the drawings. The present disclosure, however, is not limited by the embodiments described below. In addition, throughout the drawings, the same components are denoted by the same reference numerals.

First Embodiment

Schematic Structure of Medical Observation System

FIG. 1 is a diagram illustrating a schematic structure of a medical observation system 1 according to a first embodiment.

The medical observation system 1 is a device used in the medical fields for observing a subject such as the inside of a living body. As illustrated in FIG. 1, this medical observation system 1 includes an insertion unit 2, a light source device 3, a light guide 4, a camera head 5, a first transmission cable 6, a display device 7, a second transmission cable 8, a control device 9, and a third transmission cable 10.

The insertion unit 2 includes a rigid endoscope. That is to say, the insertion unit 2 is rigid or at least a part of the insertion unit 2 is flexible. The insertion unit 2 has a thin and long shape and is to be inserted into a living body. In this insertion unit 2, an optical system including one or a plurality of lenses for condensing a subject image is provided.

To the light source device 3, one end of the light guide 4 is connected. The light source device 3 is controlled by the control device 9 to supply light for illuminating the inside of the living body to the one end of the light guide 4.

The light guide 4 has one end detachably connected to the light source device 3 and the other end detachably connected to the insertion unit 2. The light guide 4 transmits the light, which is supplied from the light source device 3, from the one end to the other end and supplies the light to the insertion unit 2. The light supplied to the insertion unit 2 is emitted from the end of the insertion unit 2 to be delivered into the living body. The light reflected in the living body (subject image) is condensed by the optical system in the insertion unit 2.

The camera head 5 is detachably connected to a base end of the insertion unit 2 (eyepiece portion 21 (FIG. 1)). The camera head 5 is controlled by the control device 9 to image the subject image condensed in the insertion unit 2 and output an image signal (RAW signal) obtained by the imaging. The image signal is, for example, an image signal of 4K or more.

The detailed structure of the camera head 5 will be described below.

The first transmission cable 6 has one end detachably connected to the control device 9 through a connector CN1 (FIG. 1) and the other end detachably connected to the camera head 5 through a connector CN2 (FIG. 1). The first transmission cable 6 transmits the image signal, which is output from the camera head 5, to the control device 9 and transmits a control signal, a synchronous signal, a clock, power, and the like, which are output from the control device 9, to the camera head 5.

Note that the transmission of the image signal from the camera head 5 to the control device 9 through the first transmission cable 6 may be either optical or electrical. This similarly applies to the transmission of the control signal, the synchronous signal, and the clock from the control device 9 to the camera head 5 through the first transmission cable 6.

The display device 7 is formed of a display including liquid crystals or organic EL (Electro Luminescence), for example, and displays an image based on a video signal processed in the control device 9.

The second transmission cable 8 has one end detachably connected to the display device 7 and the other end detachably connected to the control device 9. The second transmission cable 8 transmits the video signal processed in the control device 9 to the display device 7.

The control device 9 has a function as a medical signal processing device according to the present disclosure. This control device 9 includes a central processing unit (CPU) or the like, and collectively controls the operation of the light source device 3, the camera head 5, and the display device 7.

The detailed structure of the control device 9 will be described below.

The third transmission cable 10 has one end detachably connected to the light source device 3 and the other end detachably connected to the control device 9. The third transmission cable 10 transmits the control signal from the control device 9 to the light source device 3.

Structure of Camera Head

Next, a structure of the camera head 5 is described.

FIG. 2 is a block diagram illustrating a structure of the camera head 5 and the control device 9.

In FIG. 2, for the convenience of description, the illustration of the connectors CN1 and CN2 between the control device 9 and the camera head 5, and the first transmission cable 6 and the connectors between the control device 9 and the display device 7, and the second transmission cable 8 is omitted.

The camera head 5 includes a lens unit 51, an iris 52, a driving unit 53, an imaging unit 54, and a communication unit 55 as illustrated in FIG. 2.

The lens unit 51 includes one or a plurality of lenses movable along an optical axis, and images the subject image condensed in the insertion unit 2 on an imaging surface of the imaging unit 54 (an imaging element 541). The lens unit 51 moreover includes an optical zoom mechanism (not illustrated) for changing the angle of view by moving the one or the plurality of lenses, or a focus mechanism (not illustrated) for changing the focal point.

The iris 52 adjusts the exposure by limiting the incidence amount of light condensed by the lens unit 51.

The driving unit 53 is controlled by the control device 9 to operate the optical zoom mechanism or the focus mechanism so as to change the angle of view or the focal point of the lens unit 51. In addition, the driving unit 53 is controlled by the control device 9 to adjust the amount of light to enter the imaging unit 54 by driving the iris 52.

Figure 3A:
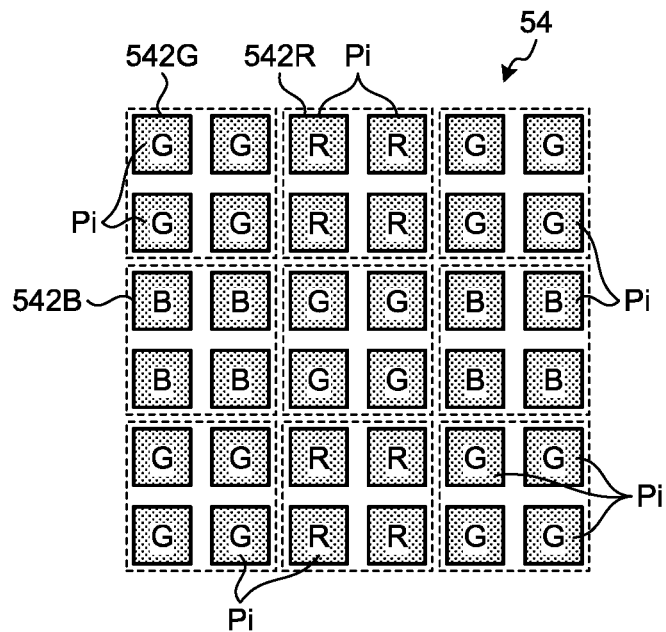
FIG. 3A is a schematic diagram illustrating the arrangement of pixels of an imaging element and describing a normal mode.
Figure 3B:
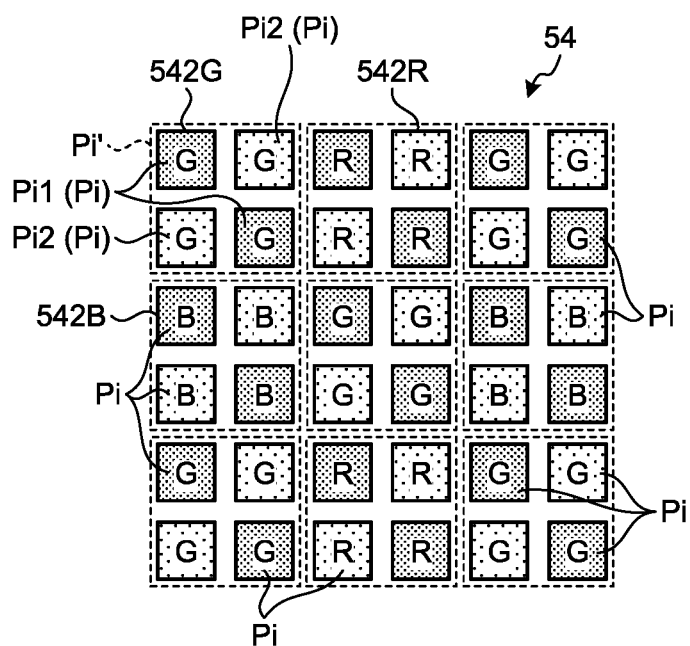
FIG. 3B is a schematic diagram illustrating the arrangement of pixels of the imaging element and describing an HDR mode.
Figure 3C:
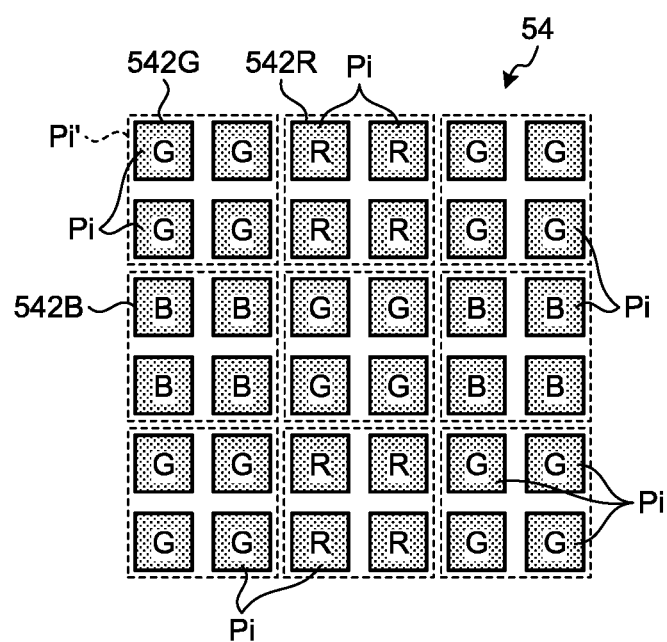
FIG. 3C is a schematic diagram illustrating the arrangement of pixels of the imaging element and describing a high-sensitivity mode.

FIG. 3A to FIG. 3C are schematic diagrams illustrating the arrangement of pixels Pi of the imaging element 541. Specifically, FIG. 3A is a diagram to describe a normal mode, FIG. 3B is a diagram to describe an HDR mode, and FIG. 3C is a diagram to describe a high-sensitivity mode.

The imaging unit 54 is controlled by the control device 9 to be driven in any of the normal mode, the HDR mode, and the high-sensitivity mode, and image the inside of the living body. This imaging unit 54 is formed of a sensor chip in which the imaging element 541 (FIG. 2) such as a complementary metal oxide semiconductor (CMOS) for receiving the subject image condensed in the insertion unit 2 and imaged by the lens unit 51 and converting the received image into an electric signal, a signal processing unit (not illustrated) that performs signal processing (A/D conversion, for example) on the electric signal (analog signal) from the imaging element 541 and outputs the image signal, and the like are integrated. The imaging unit 54 outputs the image signal (digital signal) after the A/D conversion. The aforementioned signal processing unit (not illustrated) may alternatively be formed separately without being integrated with the imaging element 541.

Here, the imaging surface (light receiving surface) of the imaging element 541 has a color filter 542 (FIG. 2) in which three filters are arranged in a predetermined arrangement. The three filters are provided in accordance with the wavelength bands of light to transmit (red (R), green (G), and blue (B)).

More specifically, as illustrated in FIG. 3A to FIG. 3C, the color filter 542 includes an R filter 542R to transmit the light with a red wavelength band, a B filter 542B to transmit the light with a blue wavelength band, and a G filter 542G to transmit the light with a green wavelength band. In FIG. 3A to FIG. 3C, the pixels Pi having the R filter 542R are given a letter R, the pixels Pi having the G filter 542G are given a letter G, and the pixels Pi having the B filter 542B are given a letter B.

That is to say, the image signal generated by the imaging unit 54 includes the component information (pixel signal) of any of R, G, and B corresponding to the R filter 542R, G filter 542G, and B filter 542B for each pixel Pi.

In the first embodiment, as indicated by dashed lines in FIG. 3A to FIG. 3C, all the pixels of the imaging element 541 are sectioned into a plurality of sets: one set consists of four adjacent pixels Pi (two pixels Pi in the same row and two pixels Pi in the same column constitute one set of four pixels Pi). In regard to each of the R filter 542R, the G filter 542G, or the B filter 542B, the four pixels Pi included in one set have the same filter, and when the one set (four pixels Pi) is regarded as one pixel, the filters are disposed in the Bayer array.

Next, description is made of the normal mode, the HDR mode, and the high-sensitivity mode with reference to FIG. 3A to FIG. 3C. In FIG. 3A to FIG. 3C, the exposure time of each pixel Pi (the intervals of releasing the electronic shutter) is expressed by the depth of color of each pixel Pi (the exposure time is shorter as the color is lighter).

In the normal mode, the exposure time of all the pixels of the imaging element 541 is set to be the same (for example, if the frame rate is 60 fps, the exposure time is 1/60 seconds) as illustrated in FIG. 3A. The imaging unit 54 outputs pixel signals, output from respective pixels Pi, each serving as the pixel signal of one pixel. That is to say, the normal mode is the driving mode for driving the imaging unit 54 normally.

In the HDR mode, in all the pixels of the imaging element 541, the exposure time of at least one pixel Pi of the four pixels Pi included in one set is different from the exposure time of the other pixels Pi. More specifically, in all the pixels of the imaging element 541, the exposure time of two pixels Pi1, which are positioned at the opposite corners in the four pixels Pi included in one set, is the same (for example, if the frame rate is 60 fps, the exposure time is 1/60 seconds) as illustrated in FIG. 3B. In all the pixels of the imaging element 541, the exposure time of the other two pixels Pi2, which are positioned at the opposite corners in the four pixels Pi included in one set, is the same (for example, if the frame rate is 60 fps, the exposure time is 1/120 seconds) but shorter than the exposure time of the pixels Pi1. Then, the imaging unit 54 outputs addition pixel signals obtained by adding up the pixel signals of the four pixels Pi1 and Pi2 included in one set, each serving as the pixel signal of one pixel Pi' for each set (FIG. 3B). That is to say, the HDR mode is the driving mode that enables a wide dynamic range by increasing the sensitivity when the light incidence amount is small and decreasing the sensitivity when the light incidence amount is large in a manner that the pixel signals of four pixels Pi1 and Pi2 with the different exposure times in one set are added up.

In the high-sensitivity mode, the exposure time of all the pixels of the imaging element 541 is set to be the same as illustrated in FIG. 3C (for example, if the frame rate is 60 fps, the exposure time is 1/60 seconds). The imaging unit 54 outputs addition pixel signals obtained by adding up the pixel signals of the four pixels Pi included in one set, each serving as the pixel signal of one pixel Pi' (FIG. 3C) for each set. That is to say, the high-sensitivity mode is the driving mode in which the sensitivity may be increased when the light incidence amount is small, by increasing the signal level per pixel Pi' by adding up the pixel signals of the four pixels Pi with the same exposure time in one set.

The communication unit 55 functions as a transmitter that transmits the image signal output from the imaging unit 54 to the control device 9 through the first transmission cable 6. This communication unit 55 includes, for example, a high-speed serial interface that communicates the image signal at a transmission rate of 1 Gbps or more between the communication unit 55 and the control device 9 through the first transmission cable 6.

Structure of Control Device

Next, the structure of the control device 9 is described with reference to FIG. 2.

As illustrated in FIG. 2, the control device 9 includes a communication unit 91, a signal processing unit 92, a display control unit 93, a control unit 94, an input unit 95, an output unit 96, and a storage unit 97.

The communication unit 91 functions as a receiver that receives the image signal output from the camera head 5 (communication unit 55) through the first transmission cable 6. This communication unit 91 includes, for example, a high-speed serial interface that communicates the image signal at a transmission rate of 1 Gbps or more between the communication unit 55 and the communication unit 91.

The signal processing unit 92 is controlled by the control unit 94 to process the image signal (RAW signal) output from the camera head 5 (communication unit 55) and received in the communication unit 91. This signal processing unit 92 includes a RAW processing unit 921, an RGB processing unit 922, and a YC processing unit 923 as illustrated in FIG. 2.

The RAW processing unit 921 performs the RAW process such as a demosaic process on the image signal (RAW signal) received in the communication unit 91, and converts the RAW signal (image signal) into the RGB signal (image signal).

The RGB processing unit 922 performs the RGB process such as the white balance adjustment, the RGB gamma-correction, and the YC conversion (converting the RGB signal into the luminance signal and the color difference signal (Y, $C_B/C_R$ signals)) on the image signal (RGB signal) subjected to the RAW process in the RAW processing unit 921.

The YC processing unit 923 processes the image signal (Y, $C_B/C_R$ signals) subjected to the RGB process in the RGB processing unit 922. This YC processing unit 923 includes a Y gamma-correction unit 9231 and a histogram calculation unit 9232 as illustrated in FIG. 2.

The Y gamma-correction unit 9231 operates in any of the first to the fourth operation modes set in the control unit 94, and performs the Y gamma-correction on the luminance signal (Y signal) included in the image signal (Y, $C_B/C_R$ signals) subjected to the RGB process in the RGB processing unit 922. Here, the Y gamma-curve in the Y gamma-correction is different in each of the first to the fourth modes.

The histogram calculation unit 9232 calculates the histogram of the luminance signal (Y signal) for each pixel on the basis of the luminance signal (Y signal) included in the image signal (Y, $C_B/C_R$ signals) subjected to the RGB process in the RGB processing unit 922.

The display control unit 93 generates the video signal for display from the luminance signal (Y signal) subjected to the Y gamma-correction in the Y gamma-correction unit 9231, and the color difference signal ($C_B/C_R$ signal) included in the image signal (Y, $C_B/C_R$ signals) subjected to the RGB process in the RGB processing unit 922. The display control unit 93 outputs the video signal to the display device 7 through the second transmission cable 8.

The control unit 94 is formed of a CPU or the like, for example, and controls the operation of the light source device 3 and the camera head 5 by outputting the control signal through the first transmission cable 6 and the third transmission cable 10, and controls the operation of the entire control device 9. This control unit 94 includes a mode setting unit 941 and an imaging control unit 942 as illustrated in FIG. 2.

The mode setting unit 941 sets the driving mode of the imaging unit 54 to any of the normal mode, the HDR mode, and the high-sensitivity mode on the basis of the histogram calculated by the histogram calculation unit 9232. In addition, the mode setting unit 941 sets the operation mode of the Y gamma-correction unit 9231 to any of the first to the fourth operation modes on the basis of the histogram.

The imaging control unit 942 outputs the control signal to the imaging unit 54 through the first transmission cable 6, and drives the imaging unit 54 in the driving mode set in the mode setting unit 941.

The input unit 95 is formed of an operation device such as a mouse, a keyboard, or a touch panel, and receives the user's operation.

The output unit 96 is formed of a speaker, a printer, or the like, and outputs various kinds of information.

The storage unit 97 stores programs to be executed by the control unit 94, the information necessary for the processing in the control unit 94, and the like.

Operation of Control Device

Next, the operation of the control device 9 is described.

Figure 4:
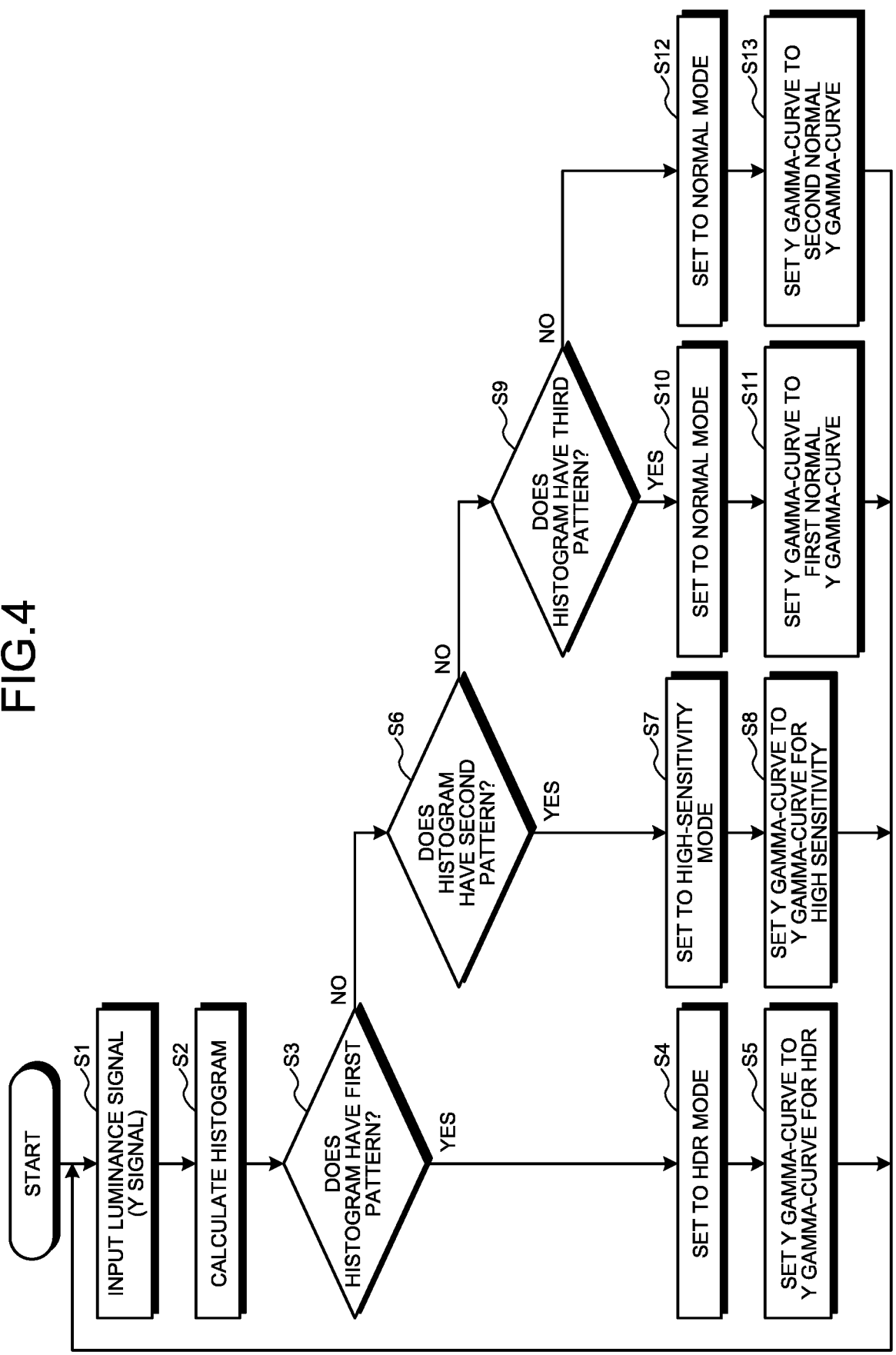
FIG. 4 is a flowchart of the operation of the control device.

FIG. 4 is a flowchart of the operation of the control device 9.

Note that the operation of the YC processing unit 923, the mode setting unit 941, and the imaging control unit 942 is mainly described below.

First, the luminance signal (Y signal) included in the image signal (Y, $C_B/C_R$ signals) subjected to the RGB process in the RGB processing unit 922 is input to the histogram calculation unit 9232 (Step S1), and the histogram calculation unit 9232 calculates the histogram of the luminance signal (Y signal) for each pixel (Step S2).

After Step S2, the mode setting unit 941 determines whether the histogram calculated at Step S2 is the histogram of a first pattern (Step S3).

Figure 5A:
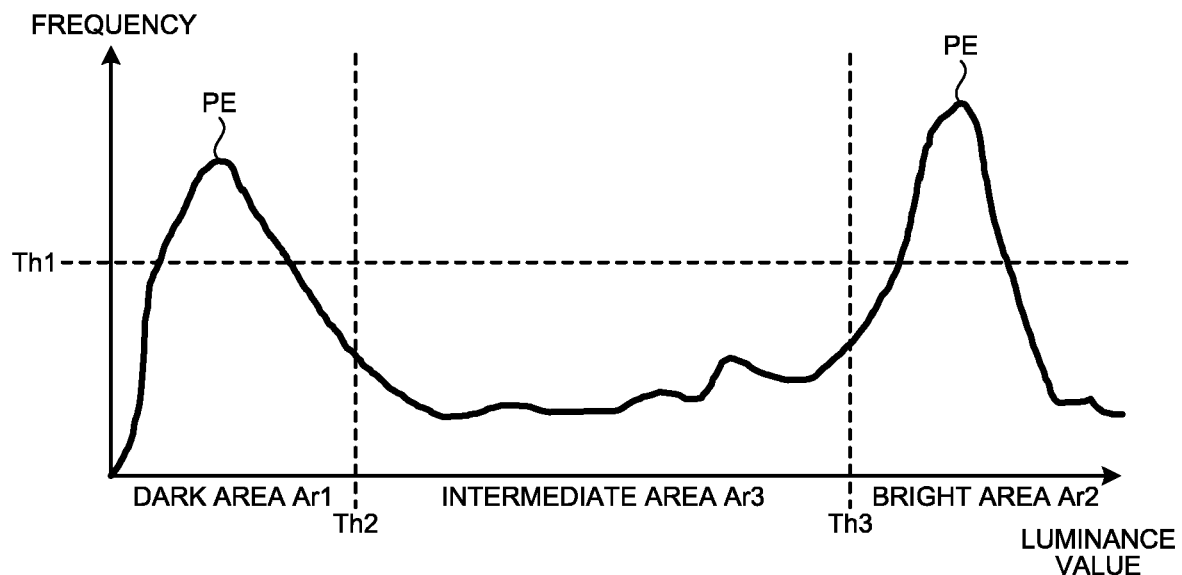
FIG. 5A is a diagram illustrating one example of the histogram of a first pattern.

FIG. 5A is a diagram illustrating one example of the histogram of the first pattern.

In FIG. 5A, the peak PE is the peak in which the frequency is more than a first threshold Th1. In regard to the luminance values, the area less than or equal to a second threshold Th2 is a dark area Ar1, the area more than or equal to a third threshold Th3, which is higher than the second threshold Th2, is a bright area Ar2, and the area between the dark area Ar1 and the bright area Ar2 is an intermediate area Ar3. This similarly applies to FIG. 6A, FIG. 7A, and FIG. 8A.

For example, as illustrated in FIG. 5A, the histogram of the first pattern contains at least two peaks PE. The at least two peaks PE exist in the dark area Ar1 and the bright area Ar2.

That is to say, at Step S3, the mode setting unit 941 detects the three most frequent peaks PE from the histogram calculated at Step S2. The mode setting unit 941 determines whether at least two peaks PE among the three detected peaks PE exist in the dark area Ar1 and the bright area Ar2. Based on this determination result, the mode setting unit 941 determines whether the histogram calculated at Step S2 is the histogram of the first pattern.

If it is determined that the histogram is the histogram of the first pattern (Yes at Step S3), the mode setting unit 941 sets the driving mode of the imaging unit 54 to the HDR mode (Step S4). Then, the imaging control unit 942 outputs the control signal to the imaging unit 54 through the first transmission cable 6, and drives the imaging unit 54 in the HDR mode.

After Step S4, the mode setting unit 941 sets the operation mode of the Y gamma-correction unit 9231 to the first operation mode, and sets the Y gamma-curve in the Y gamma-correction to the Y gamma-curve for the HDR (Step S5). The Y gamma-correction unit 9231 performs the Y gamma-correction by the Y gamma-curve for HDR, on the luminance signal (Y signal) included in the image signal (Y, $C_B/C_R$ signals) subjected to the RGB process in the RGB processing unit 922. After Step S5, the control device 9 returns the process to Step S1.

Figure 5B:
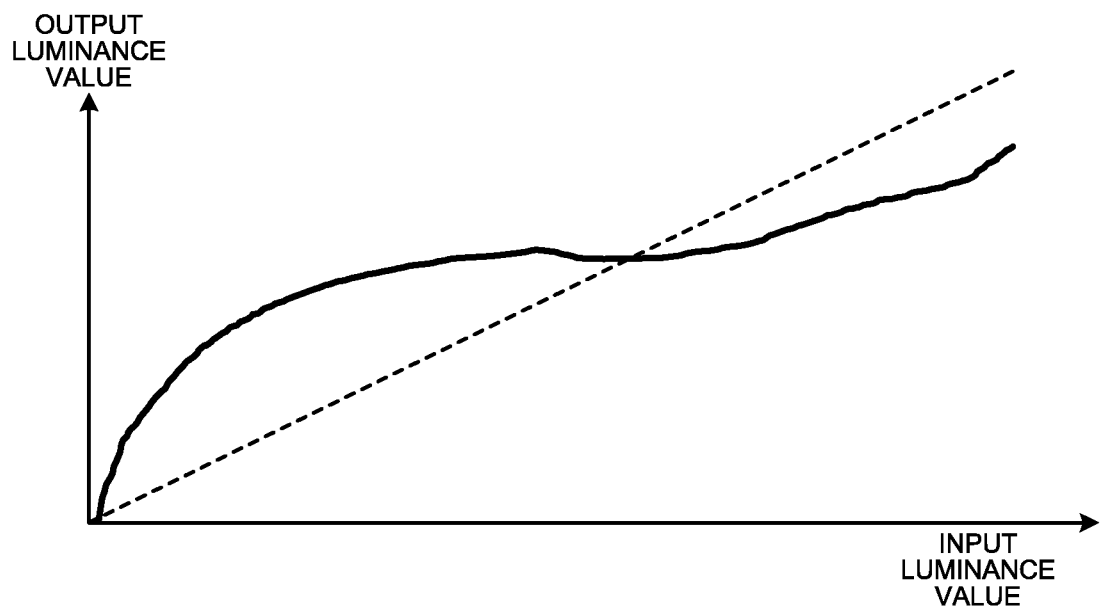
FIG. 5B is a diagram illustrating one example of the Y gamma-curve for HDR.

FIG. 5B is a diagram illustrating one example of the Y gamma-curve for HDR.

For example, the Y gamma-curve for HDR is the gamma-curve for increasing the luminance value of the pixel in which the luminance value of the input luminance signal (Y signal) is low and decreasing the luminance value of the pixel in which the luminance value is high as illustrated in FIG. 5B.

If it is determined that the histogram calculated at Step S2 is not the histogram of the first pattern (No at Step S3), the mode setting unit 941 determines whether the histogram calculated at Step S2 is the histogram of a second pattern (Step S6).

Figure 6A:
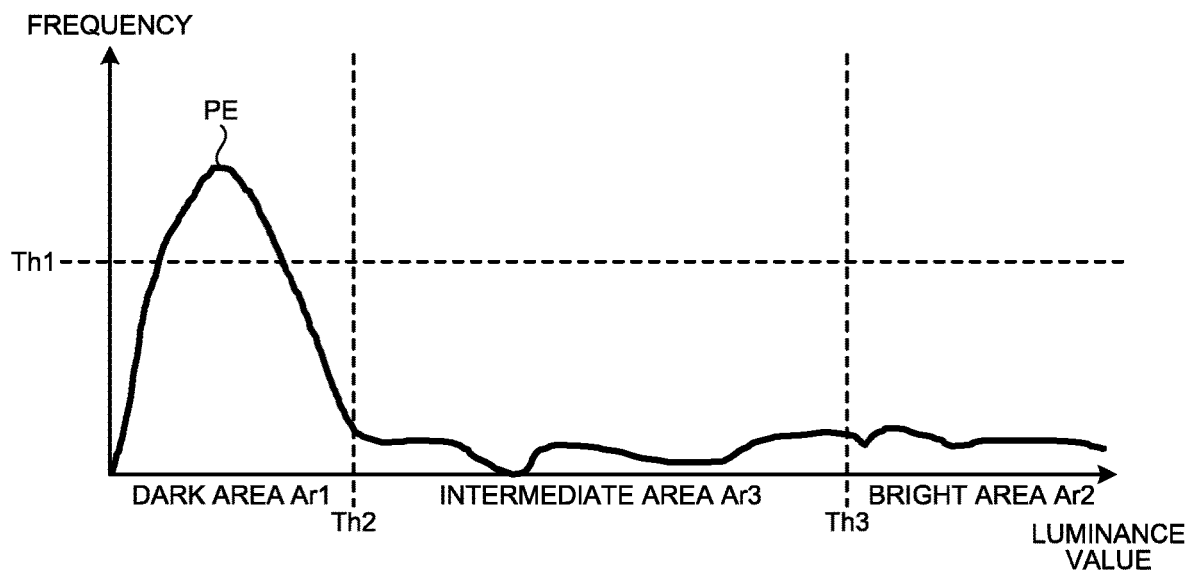
FIG. 6A is a diagram illustrating one example of the histogram of a second pattern.

FIG. 6A is a diagram illustrating one example of the histogram of the second pattern.

For example, the histogram of the second pattern contains at least one peak PE as illustrated in FIG. 6A. The at least one peak PE does not exist in the bright area Ar2 but exists in the dark area Ar1.

That is to say, at Step S6, the mode setting unit 941 detects the three most frequent peaks PE from the histogram calculated at Step S2. The mode setting unit 941 determines whether none of the three detected peaks PE exists in the bright area Ar2 and at least one peak PE of the three detected peaks PE exists in the dark area Ar1. Thus, the mode setting unit 941 determines whether the histogram calculated at Step S2 is the histogram of the second pattern.

If it is determined that the histogram is the histogram of the second pattern (Yes at Step S6), the mode setting unit 941 sets the driving mode of the imaging unit 54 to the high-sensitivity mode (Step S7). Then, the imaging control unit 942 outputs the control signal to the imaging unit 54 through the first transmission cable 6 to drive the imaging unit 54 in the high-sensitivity mode.

After Step S7, the mode setting unit 941 sets the operation mode of the Y gamma-correction unit 9231 to the second operation mode, and sets the Y gamma-curve in the Y gamma-correction to the Y gamma-curve for the high sensitivity (Step S8). Then, the Y gamma-correction unit 9231 performs the Y gamma-correction by the Y gamma-curve for the high sensitivity, on the luminance signal (Y signal) included in the image signal (Y, $C_B/C_R$ signals) subjected to the RGB process in the RGB processing unit 922. After Step S8, the control device 9 returns the process to Step S1.

Figure 6B:
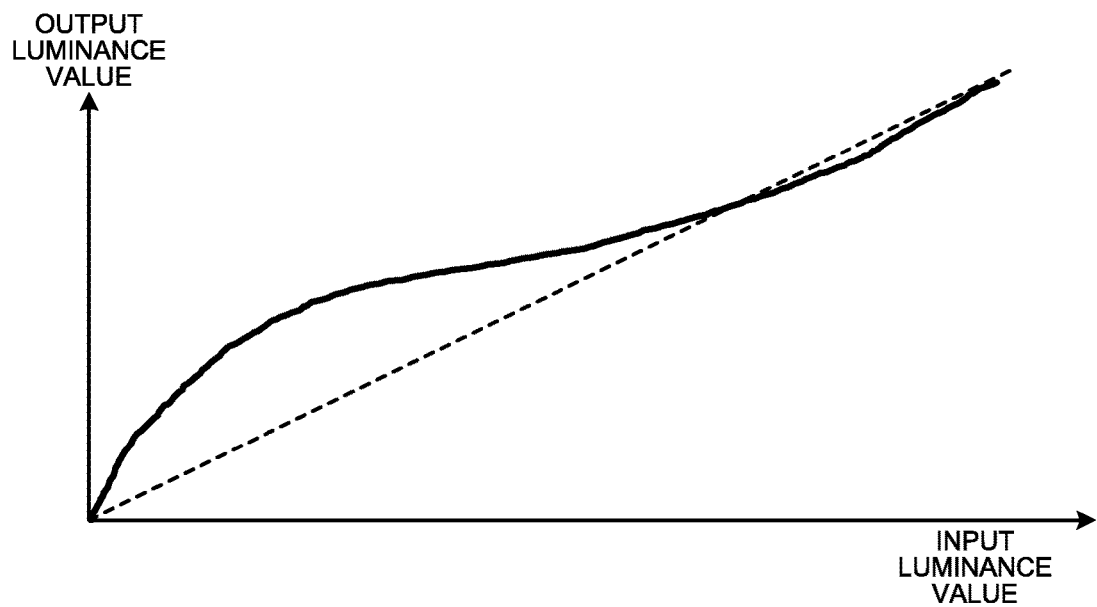
FIG. 6B is a diagram illustrating one example of the Y gamma-curve for high sensitivity; p

FIG. 6B is a diagram illustrating one example of the Y gamma-curve for the high sensitivity.

For example, the Y gamma-curve for the high sensitivity is the gamma-curve for not correcting the pixel in which the luminance value of the input luminance signal (Y signal) is high and increasing the luminance value of the pixel with a low luminance value, as illustrated in FIG. 6B.

In addition, if it is determined that the histogram is not the histogram of the second pattern (No at Step S6), the mode setting unit 941 determines whether the histogram calculated at Step S2 is the histogram of a third pattern (Step S9).

Figure 7A:
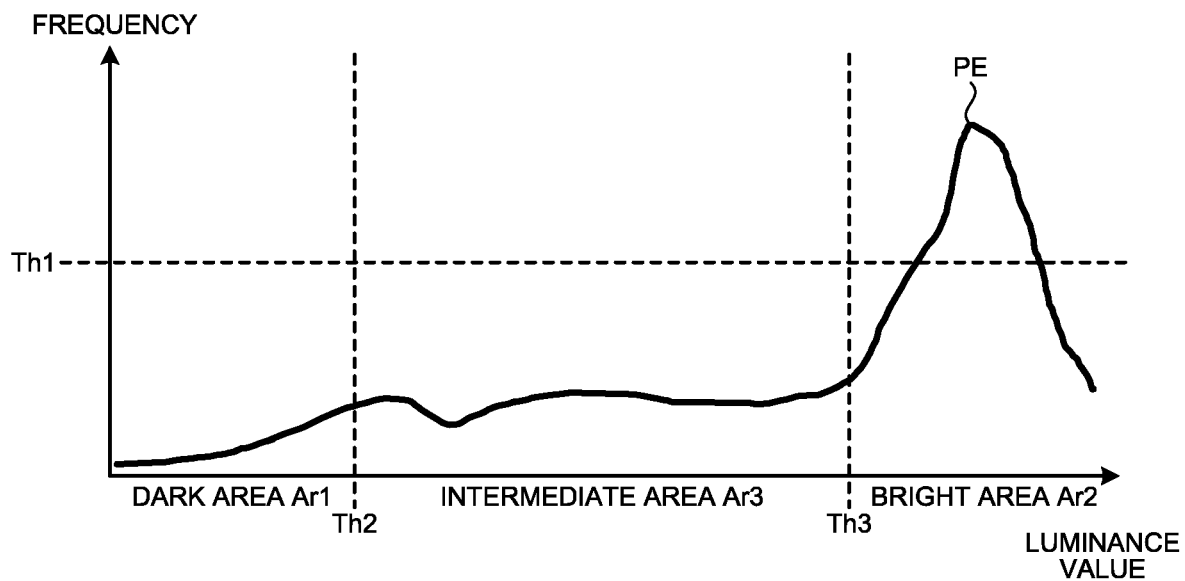
FIG. 7A is a diagram illustrating one example of the histogram of a third pattern.

FIG. 7A is a diagram illustrating one example of the histogram of the third pattern.

For example, the histogram of the third pattern contains at least one peak PE as illustrated in FIG. 7A. The at least one peak PE does not exist in the dark area Ar1 but exists in the bright area Ar2.

That is to say, at Step S9, the mode setting unit 941 detects the three most frequent peaks PE from the histogram calculated at Step S2. The mode setting unit 941 determines whether none of the three detected peaks PE exists in the dark area Ar1 and at least one peak PE of the three detected peaks PE exists in the bright area Ar2. Thus, the mode setting unit 941 determines whether the histogram calculated at Step S2 is the histogram of the third pattern.

If it is determined that the histogram is the histogram of the third pattern (Yes at Step S9), the mode setting unit 941 sets the driving mode of the imaging unit 54 to the normal mode (Step S10). Then, the imaging control unit 942 outputs the control signal to the imaging unit 54 through the first transmission cable 6 to drive the imaging unit 54 in the normal mode.

After Step S10, the mode setting unit 941 sets the operation mode of the Y gamma-correction unit 9231 to the third operation mode, and sets the Y gamma-curve in the Y gamma-correction to a first normal Y gamma-curve (Step S11). Then, the Y gamma-correction unit 9231 performs the Y gamma-correction by the first normal Y gamma-curve, on the luminance signal (Y signal) included in the image signal (Y, $C_B/C_R$ signals) subjected to the RGB process in the RGB processing unit 922. After Step S11, the control device 9 returns the process to Step S1.

Figure 7B:
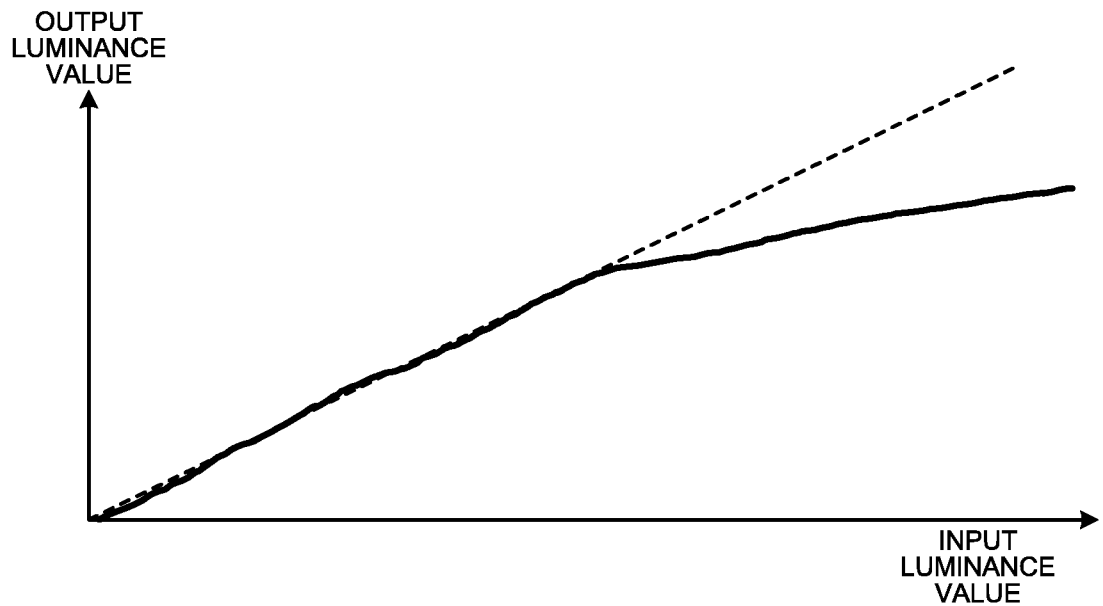
FIG. 7B is a diagram illustrating one example of a first normal Y gamma-curve.

FIG. 7B is a diagram illustrating one example of the first normal Y gamma-curve.

For example, the first normal Y gamma-curve is the gamma-curve for not correcting the pixel in which the luminance value of the input luminance signal (Y signal) is low and decreasing the luminance value of the pixel with a high luminance value, as illustrated in FIG. 7B.

In addition, if it is determined that the histogram is not the histogram of the third pattern (No at Step S9), the mode setting unit 941 determines that the histogram calculated at Step S2 is the histogram of a fourth pattern.

Figure 8A:
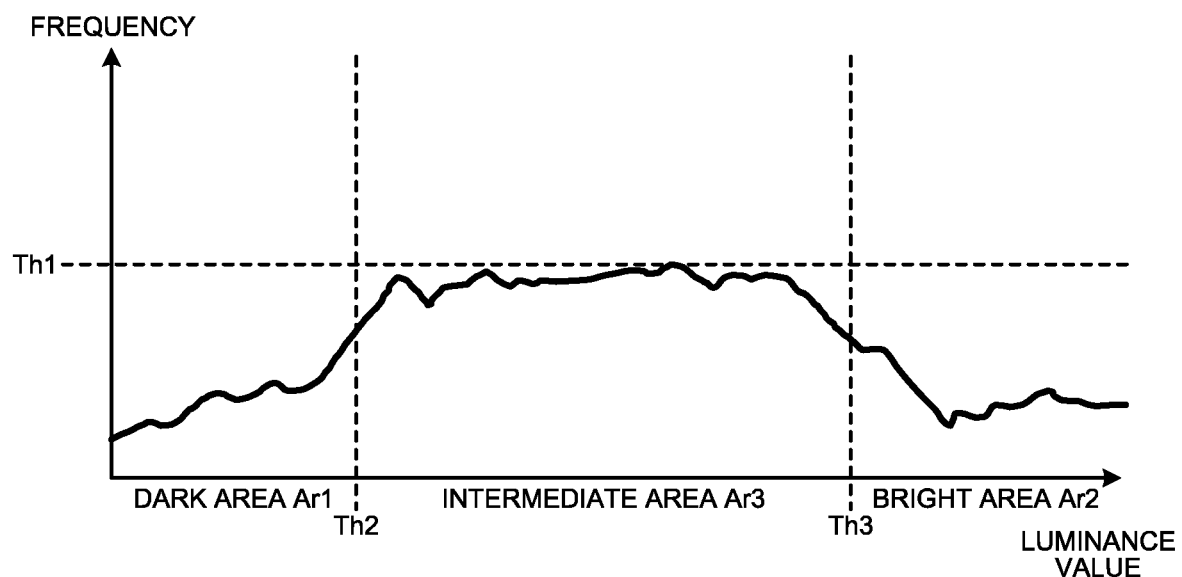
FIG. 8A is a diagram illustrating one example of the histogram of a fourth pattern.

FIG. 8A is a diagram illustrating one example of the histogram of the fourth pattern.

For example, the histogram of the fourth pattern does not contain the peak PE or even if it contains, the peak PE exists in neither the dark area Ar1 nor the bright area Ar2 as illustrated in FIG. 8A.

Then, the mode setting unit 941 sets the driving mode of the imaging unit 54 to the normal mode (Step S12). The imaging control unit 942 outputs the control signal to the imaging unit 54 through the first transmission cable 6 to drive the imaging unit 54 in the normal mode.

After Step S12, the mode setting unit 941 sets the operation mode of the Y gamma-correction unit 9231 to the fourth operation mode, and sets the Y gamma-curve in the Y gamma-correction to a second normal Y gamma-curve (Step S13). Then, the Y gamma-correction unit 9231 performs the Y gamma-correction by the second normal Y gamma-curve on the luminance signal (Y signal) included in the image signal (Y, $C_B/C_R$ signals) subjected to the RGB process in the RGB processing unit 922. After Step S13, the control device 9 returns the process to Step S1.

Figure 8B:
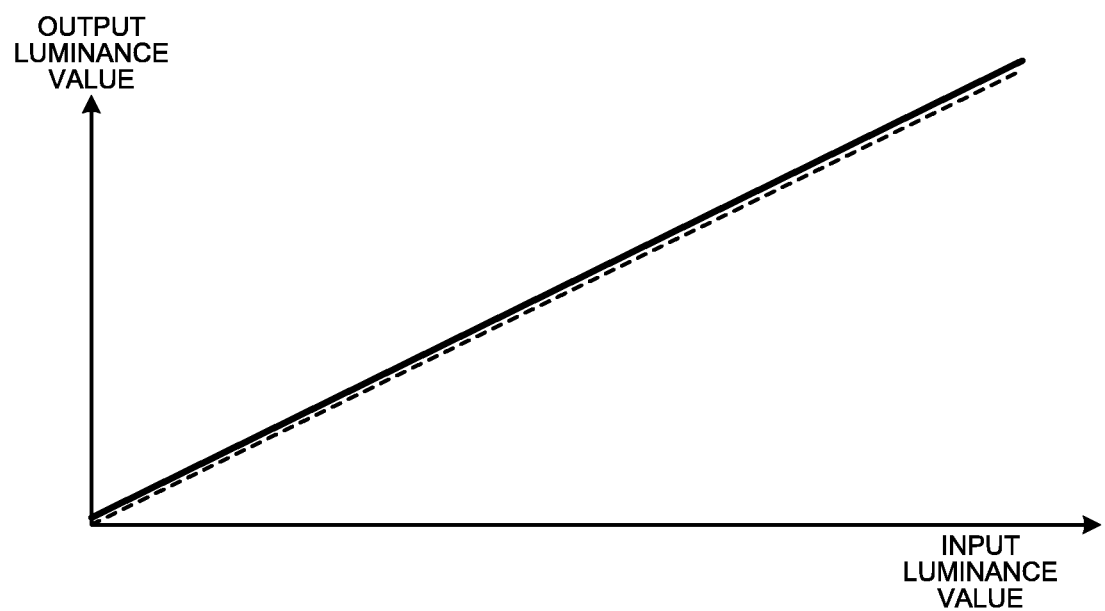
FIG. 8B is a diagram illustrating one example of a second normal Y gamma-curve.

FIG. 8B is a diagram illustrating one example of the second normal Y gamma-curve.

For example, the second normal Y gamma-curve is linear as illustrated in FIG. 8B, and in this curve, the input luminance signal (Y signal) is output directly. That is to say, in the second normal Y gamma-curve, the Y gamma-correction unit 9231 does not perform the Y gamma-correction on the luminance signal (Y signal).

According to the first embodiment described above, the following effect may be obtained.

The control device 9 according to the first embodiment includes the Y gamma-correction unit 9231 that performs the Y gamma-correction on the luminance signal (Y) for each pixel in the image obtained by the imaging unit 54.

Therefore, in the case of displaying an image not suitable for observation (for example, an image where a bright part results in white, an image where a dark part results in black, or an image where a forceps or white gauze gets in the image of a subject to make the image appear brighter as a whole), the Y gamma-correction is performed. That is to say, when the pixel has a low luminance value, the luminance value may be increased by the Y gamma-correction, and when the pixel has a high luminance value, the luminance value may be decreased by the Y gamma-correction. By the Y gamma-correction, an image suitable for observation may be displayed and the convenience may be improved.

Therefore, the control device 9 according to the first embodiment does not need to have a plurality of imaging elements with different sensitivities, and thus, the effect of improving the convenience without complicating the structure may be obtained.

In addition, the control device 9 according to the first embodiment includes the mode setting unit 941 for setting the operation mode of the Y gamma-correction unit 9231 to any of the first to fourth operation modes on the basis of the histogram of the luminance signal (Y signal) for each pixel. The Y gamma-curve in the Y gamma-correction is different in each of the first to the fourth operation modes.

Therefore, whether the image obtained by the imaging unit 54 is suitable for observation may be determined properly and the operation mode may be set in accordance with the state of the image (histogram). For example, if the image contains a large proportion of both the dark area and the bright area (FIG. 5A), the operation mode is set to the first operation mode in which the Y gamma-correction is performed by the Y gamma-curve for HDR for increasing the luminance value of the pixel in which the luminance value of the input luminance signal (Y signal) is low and decreasing the luminance value of the pixel in which the luminance value is high. In another example, if the image contains a large proportion of the dark area (FIG. 6A), the operation mode is set to the second operation mode in which the Y gamma-correction is performed by the Y gamma-curve for the high sensitivity for not correcting the pixel in which the input luminance signal (Y signal) is high and increasing the luminance value of the pixel in which the luminance value is low.

In the control device 9 according to the first embodiment, the mode setting unit 941 sets the driving mode of the imaging unit 54 to any of the normal mode, the HDR mode, and the high-sensitivity mode.

Therefore, the above-described effects may be further enhanced that an image suitable for observation may be displayed by changing the driving mode of the imaging unit 54 and changing the Y gamma-curve in accordance with the state of the image (histogram).

Second Embodiment

Next, a second embodiment will be described.

In the following description, the structures similar to those of the first embodiment are denoted by the same reference numerals and the detailed description thereof is omitted or abbreviated.

Figure 9:
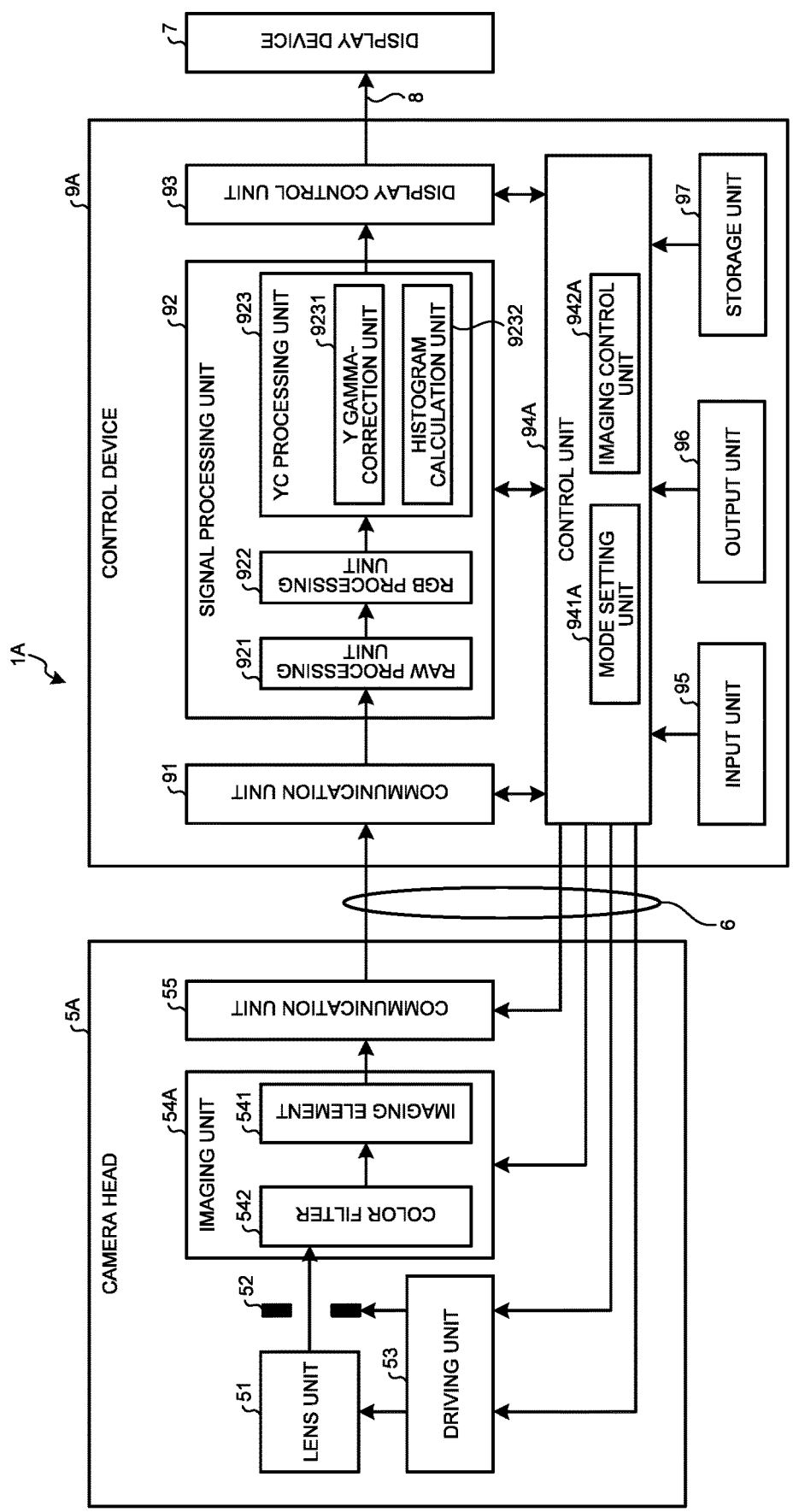
FIG. 9 is a diagram illustrating a schematic structure of a medical observation system according to a second embodiment and corresponding to FIG. 2.

FIG. 9 is a diagram illustrating a schematic structure of a medical observation system 1A according to the second embodiment and corresponding to FIG. 2.

The medical observation system 1A (a camera head 5A (an imaging unit 54A) and a control device 9A (a control unit 94A (a mode setting unit 941A and an imaging control unit 942A))) according to the second embodiment is different from the medical observation system 1 described in the first embodiment in the following points:

the imaging unit 54A is driven only in the normal mode;

the mode setting unit 941A does not set the driving mode of the imaging unit 54A and sets only the operation mode of the Y gamma-correction unit 9231; and the imaging control unit 942A outputs the control signal to the imaging unit 54A through the first transmission cable 6 to drive the imaging unit 54A in the normal mode.

That is to say, in the operation of the control device 9A according to the second embodiment, the imaging unit 54A is driven only in the normal mode (the setting of the driving mode of the imaging unit 54A is not performed); therefore, in the operation of the control device 9 described in the first embodiment (FIG. 4), Steps S4, S7, S10, and S12 are omitted.

The effects similar to those of the first embodiment described above may be obtained when the structure in which the imaging unit 54A is driven only in the normal mode is employed as described in the second embodiment.

Third Embodiment

Next, a third embodiment will be described.

In the following description, the structures similar to those of the first embodiment are denoted by the same reference numerals and the detailed description thereof is omitted or abbreviated.

Figure 10:
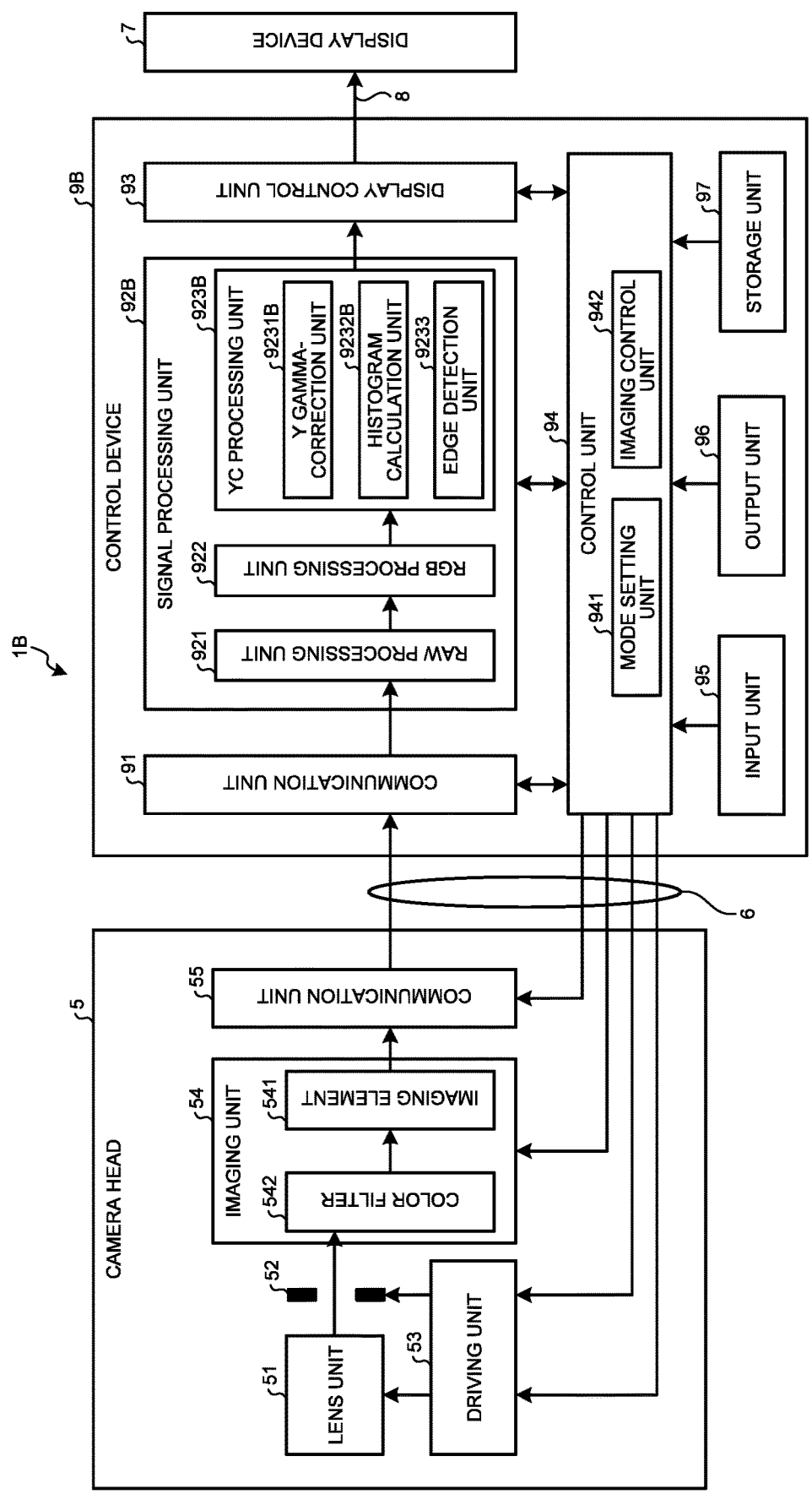
FIG. 10 is a diagram illustrating a schematic structure of a medical observation system according to a third embodiment and corresponding to FIG. 2.

FIG. 10 is a diagram illustrating a schematic structure of a medical observation system 1B according to the third embodiment and corresponding to FIG. 2.

The medical observation system 1B according to the third embodiment (a control device 9B (a signal processing unit 92B (a YC processing unit 923B))) includes an edge detection unit 9233 for performing a mask edge detection process in addition to the medical observation system 1 described in the first embodiment as illustrated in FIG. 10.

FIG. 11 is a diagram for describing the mask edge detection process. Specifically, (a) of FIG. 11 is a diagram illustrating one example of a captured image CI obtained by the imaging unit 54. (b) of FIG. 11 is a diagram expressing the distribution of the luminance values along a horizontal line L5 in the captured image CI of (a) of FIG. 11.

Here, the light reflected in the living body and condensed in the insertion unit 2 (subject image) has an approximately circular shape in cross section. Therefore, a subject image SI in the captured image CI obtained by the imaging unit 54 has an approximately circular shape as illustrated in (a) of FIG. 11. That is to say, the captured image CI includes the subject image SI and a mask area MA (the black part in (a) of FIG. 11) other than the subject image SI.

The edge detection unit 9233 detects border points BP ((a) of FIG. 11) between the subject image SI and the mask area MA by executing the mask edge detection process as below.

Specifically, the edge detection unit 9233 detects the distribution of the luminance values along a plurality of (in the third embodiment, 14) horizontal lines L1 to L14 in the captured image CI on the basis of the luminance signal (Y signal) included in the image signal (Y, $C_B/C_R$ signals) subjected to the RGB process in the RGB processing unit 922 as illustrated in (a) of FIG. 11. Here, in the captured image CI, the area of the subject image SI has the higher luminance value than the mask area MA. That is to say, for example, in the luminance distribution along the horizontal line L5, the luminance value is high between the two border points BP between the subject image SI and the mask area MA and is low in the other areas as illustrated in (b) of FIG. 11. Therefore, the edge detection unit 9233 detects the distribution of the luminance values along the horizontal lines L1 to L14 and thus, recognizes a plurality of border points BP between the subject image SI and the mask area MA. Based on the recognized plurality of border points BP, the edge detection unit 9233 recognizes the area of the subject image SI surrounded by the border points BP.

A Y gamma-correction unit 9231B according to the third embodiment performs the Y gamma-correction by any Y gamma-curve set in the mode setting unit 941 only on the luminance signal (Y signal) corresponding to the pixels in the area of the subject image SI surrounded by the border points BP recognized in the edge detection unit 9233 among the luminance signals (Y signals) included in the image signals (Y, $C_B/C_R$ signals) subjected to the RGB process in the RGB processing unit 922. The Y gamma-correction unit 9231B does not perform the Y gamma-correction on the luminance signals (Y signals) corresponding to the pixels except the area of the subject image SI surrounded by the border points BP recognized in the edge detection unit 9233.

In addition, a histogram calculation unit 9232B according to the third embodiment calculates the histogram of the luminance signal (Y signal) for each pixel in the area of the subject image SI surrounded by the border points BP recognized in the edge detection unit 9233 among the luminance signals (Y signals) included in the image signals (Y, $C_B/C_R$ signals) subjected to the RGB process in the RGB processing unit 922.

Figure 12:
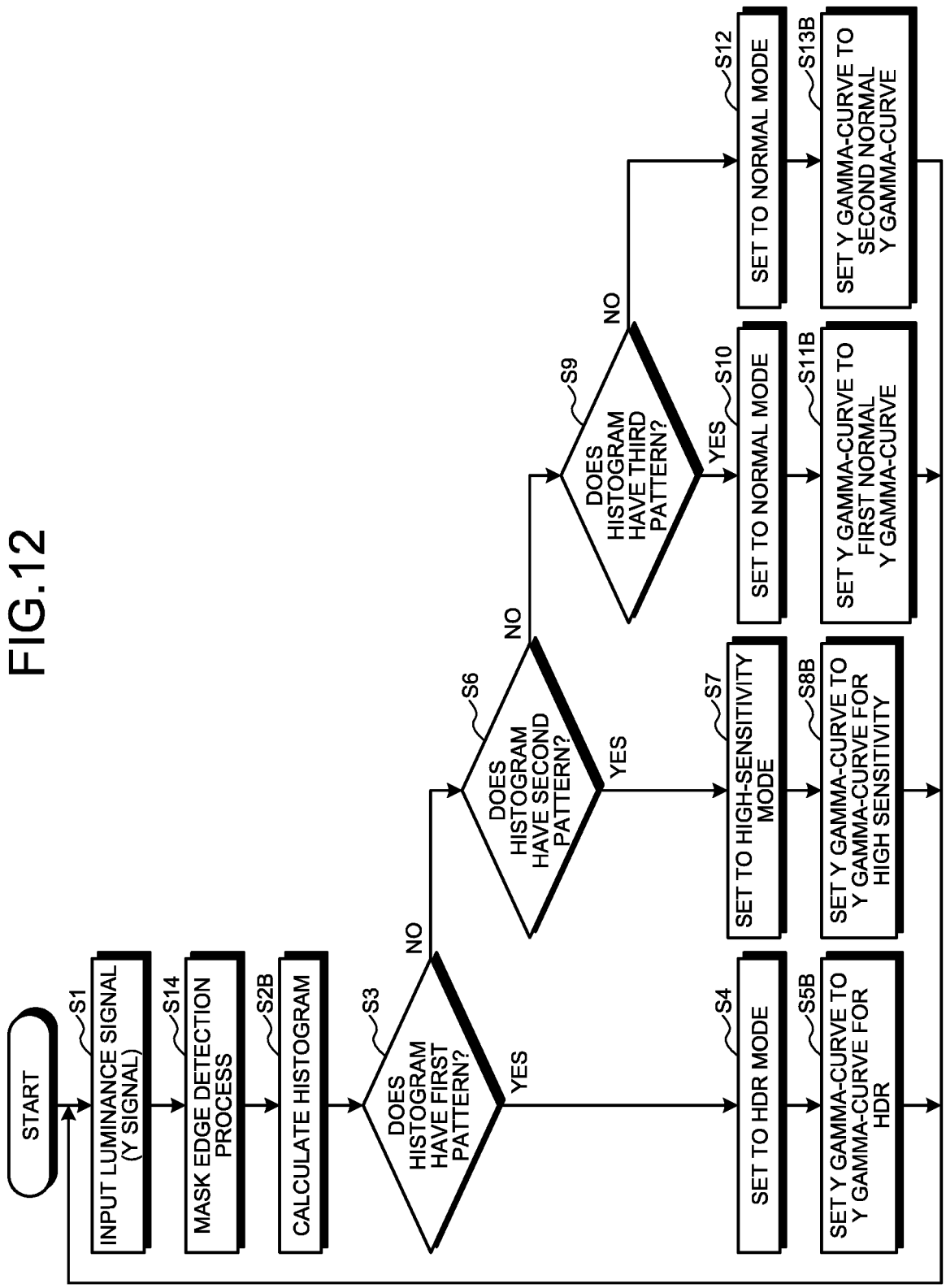
FIG. 12 is a flowchart of the operation of a control device.

FIG. 12 is a flowchart of the operation of the control device 9B.

In the operation of the control device 9B according to the third embodiment, Step S14 is added to the operation of the control device 9 described in the first embodiment (FIG. 4), and Steps S2, S5, S8, S11, and S13 in the first embodiment are replaced with Steps S2B, S5B, S8B, S11B, and S13B as illustrated in FIG. 12. Therefore, the following description is made of only Steps S14, S2B, S5B, S8B, S11B, and S13B.

Step S14 is performed after Step S1.

Specifically, the edge detection unit 9233 executes the mask edge detection process in Step S14.

At Step S2B following Step S14, the histogram calculation unit 9232B calculates the histogram of the luminance signal (Y signal) for each pixel in the area of the subject image SI surrounded by the border points BP recognized at Step S14 among the luminance signals (Y signals) included in the image signals (Y, $C_B/C_R$ signals) subjected to the RGB process in the RGB processing unit 922.

At Steps S5B, S8B, S11B, and S13B, the Y gamma-correction unit 9231B performs the Y gamma-correction by any Y gamma-curve only on the luminance signal (Y signal) corresponding to the pixels in the area of the subject image SI surrounded by the border points BP recognized at Step S14 among the luminance signals (Y signals) included in the image signals (Y, $C_B/C_R$ signals) subjected to the RGB process in the RGB processing unit 922.

According to the third embodiment described above, in addition to the effects similar to those described in the first embodiment, the following effect may be obtained.

Incidentally, performing the Y gamma-correction on the luminance signal (Y signal) corresponding to the pixels in the mask area MA may result in black floating, which is the phenomenon that the black part of the mask area MA is not displayed in black properly, and noise may stand out.

The control device 9B according to the third embodiment includes the edge detection unit 9233 for detecting the border points BP between the subject image SI and the mask area MA. The Y gamma-correction unit 9231B performs the Y gamma-correction only on the luminance signal (Y signal) corresponding to the pixels in the area of the subject image SI surrounded by the border points BP.

Therefore, black floating may be prevented in the mask area MA and the captured image CI may be displayed properly.

In the case of calculating the histogram of the luminance signal (Y signal) for each pixel with respect to all the pixels in the captured image CI, the pixels in the mask area MA with low luminance values to be displayed in black are also counted; therefore, it is difficult to determine the state (brightness) of the subject image SI properly.

In the control device 9B according to the third embodiment, the histogram calculation unit 9232B calculates the histogram of the luminance signal (Y signal) for each pixel with respect to the pixels in the area of the subject image SI surrounded by the border points BP.

Therefore, since the pixels in the mask area MA are not counted, the state (brightness) of the subject image SI may be determined properly. Thus, based on the histogram, the operation mode of the Y gamma-correction unit 9231B may be set as appropriate and moreover, the driving mode of the imaging unit 54 may be set as appropriate.

Fourth Embodiment

Next, a fourth embodiment will be described.

In the following description, the structures similar to those of the first embodiment are denoted by the same reference numerals and the detailed description thereof is omitted or abbreviated.

In contrast to the first embodiment in which the present disclosure is applied to the medical observation system 1 including the rigid endoscope (insertion unit 2), the present disclosure is applied to a medical observation system including what is called a video scope having an imaging unit at an end of the insertion unit in the fourth embodiment.

Figure 13:
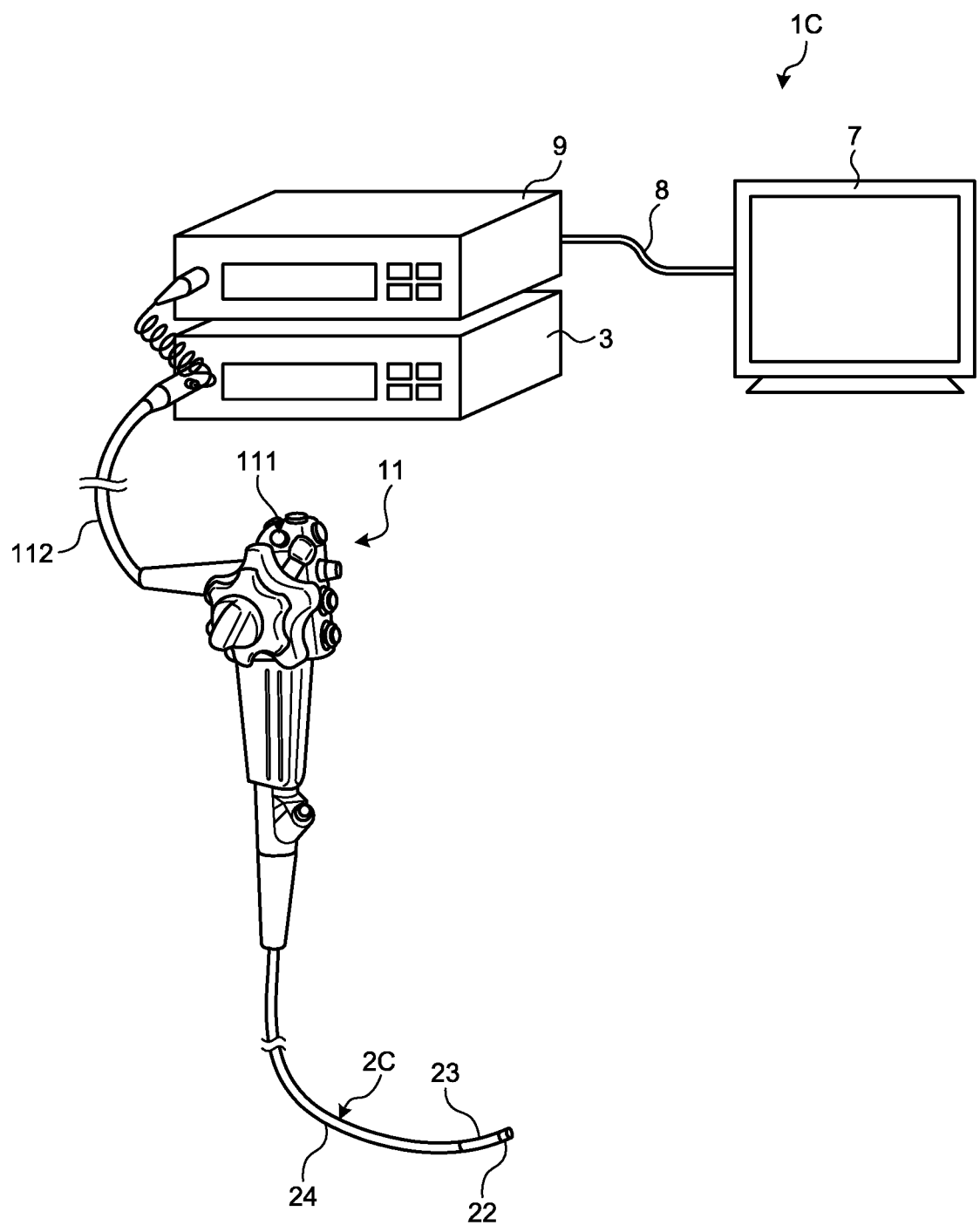
FIG. 13 is a diagram illustrating a schematic structure of a medical observation system according to a fourth embodiment.

FIG. 13 is a diagram illustrating a schematic structure of a medical observation system 1C according to the fourth embodiment.

As illustrated in FIG. 13, the medical observation system 1C according to the fourth embodiment includes: an endoscope 11 that has an insertion unit 2C inserted into a living body, images an in-vivo image of an observation target, and outputs an image signal; the light source device 3 that generates illumination light to be emitted from an end of the endoscope 11; the control device 9 that processes the image signal output from the endoscope 11; and the display device 7 that is connected to the control device 9 through the second transmission cable 8 and displays the image based on the video signal processed in the control device 9.

As illustrated in FIG. 13, the endoscope 11 includes the insertion unit 2C that is flexible and has a thin and long shape; an operation unit 111 that is connected to a base end side of the insertion unit 2C and receives the input of various manipulation signals; and a universal cord 112 that extends from the operation unit 111 in a direction different from the direction where the insertion unit 2C extends, and incorporates various cables to be connected to the light source device 3 and the control device 9.

As illustrated in FIG. 13, the insertion unit 2C includes an end part 22, a curved part 23 that is connected to a base end side of the end part 22 and has a plurality of curved pieces and may be freely curved, and a long and flexible tube part 24 that is connected to a base end side of the curved part 23.

Although not illustrated in detail, the end part 22 incorporates a structure similar to that of the imaging unit 54 described in the first embodiment. In addition, although not illustrated in detail, the operation unit 111 incorporates a structure similar to that of the communication unit 55 described in the first embodiment. The image signal obtained by the end part 22 (imaging unit) is output to the control device 9 through the operation unit 111 and the universal cord 112.

The effects similar to those of the first embodiment may be obtained when the flexible endoscope (endoscope 11) is used as described in the fourth embodiment.

Fifth Embodiment

Next, a fifth embodiment will be described.

In the following description, the structures similar to those of the first embodiment are denoted by the same reference numerals and the detailed description thereof is omitted or abbreviated.

In contrast to the first embodiment in which the present disclosure is applied to the medical observation system 1 including the rigid endoscope (insertion unit 2), the present disclosure is applied to a medical observation system including a surgical microscope that magnifies and images a predetermined viewing area of the inside of a subject (the inside of the living body) or a surface of the subject (the surface of the living body) in the fifth embodiment.

Figure 14:
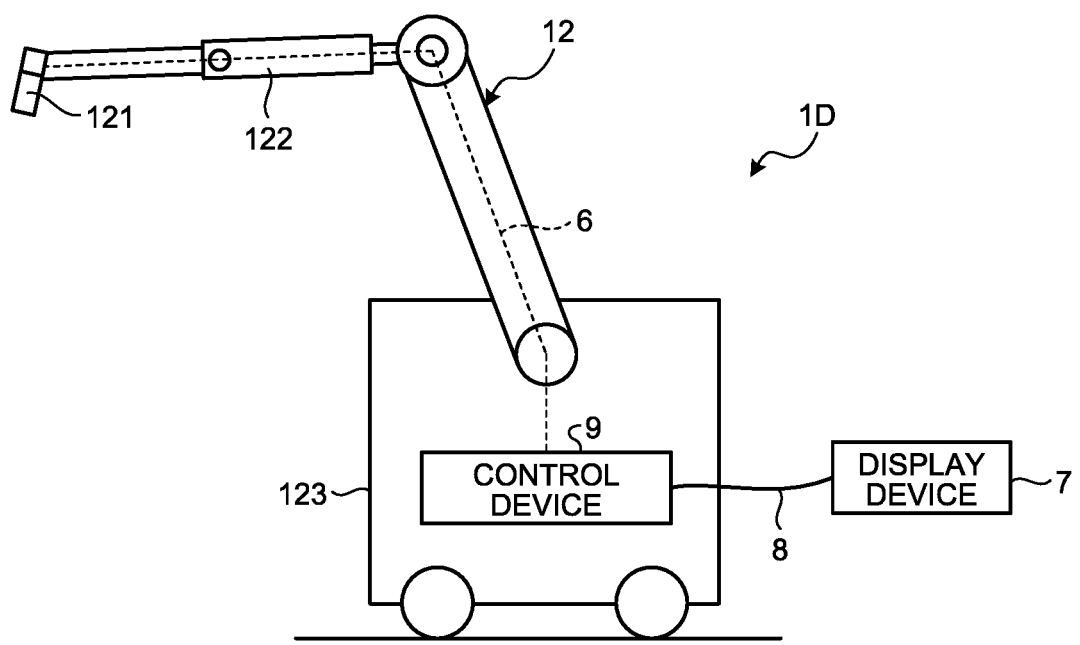
FIG. 14 is a diagram illustrating a schematic structure of a medical observation system according to a fifth embodiment.

FIG. 14 is a diagram illustrating a schematic structure of a medical observation system 1D according to the fifth embodiment.

As illustrated in FIG. 14, the medical observation system 1D according to the fifth embodiment includes: a surgical microscope 12 that images an image for observing a subject and outputs an image signal; the control device 9 that processes the image signal output from the surgical microscope 12; and the display device 7 that is connected to the control device 9 through the second transmission cable 8 and displays the image based on the video signal processed in the control device 9.

As illustrated in FIG. 14, the surgical microscope 12 includes: a microscope unit 121 that magnifies and images a microscopic part of a subject and outputs an image signal; a support unit 122 that is connected to a base end part of the microscope unit 121 and includes an arm rotatably supporting the microscope unit 121; and a base unit 123 that rotatably holds a base end part of the support unit 122 and is movable on the floor.

The control device 9 is provided to the base unit 123 as illustrated in FIG. 14.

Instead of being provided to be movable on the floor, the base unit 123 may be fixed to the ceiling, a wall surface, or the like to support the support unit 122. The base unit 123 may include a light source unit that generates illumination light to be delivered from the surgical microscope 12 to the subject.

Although not illustrated in detail, the microscope unit 121 incorporates a structure similar to that of the imaging unit 54 and the communication unit 55 described in the first embodiment. Then, the image signal obtained by the microscope unit 121 (imaging unit) is output to the control device 9 through the first transmission cable 6 disposed along the support unit 122.

The effects similar to those of the first embodiment may be obtained when the surgical microscope 12 is used as described in the fifth embodiment.

Other Embodiments

The embodiments for carrying out the present disclosure have been described so far; however, the present disclosure is not limited to the aforementioned first to the fifth embodiments.

Figure 15A:
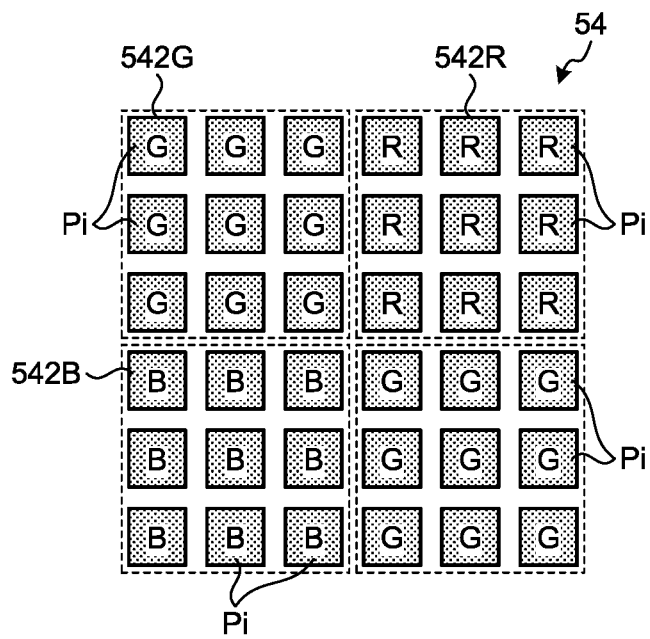
FIG. 15A is a diagram illustrating a first modification of the first to the fifth embodiments.
Figure 15B:
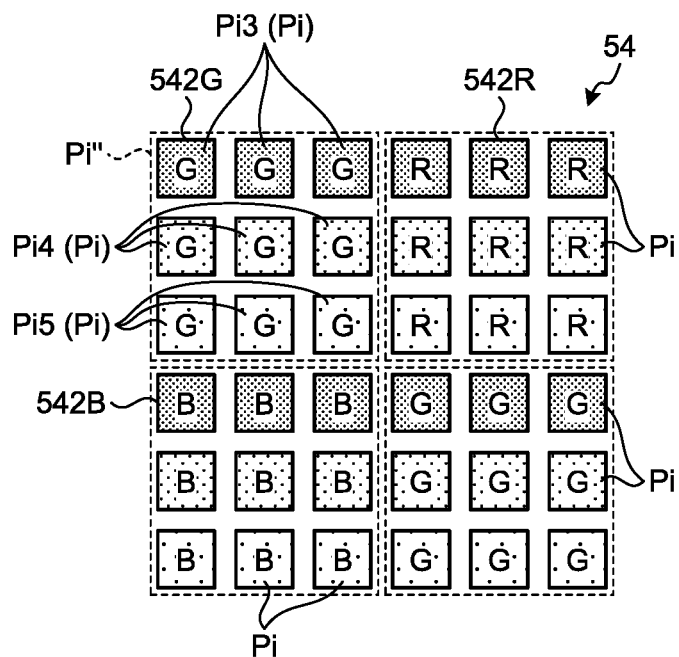
FIG. 15B is a diagram illustrating the first modification of the first to the fifth embodiments.
Figure 15C:
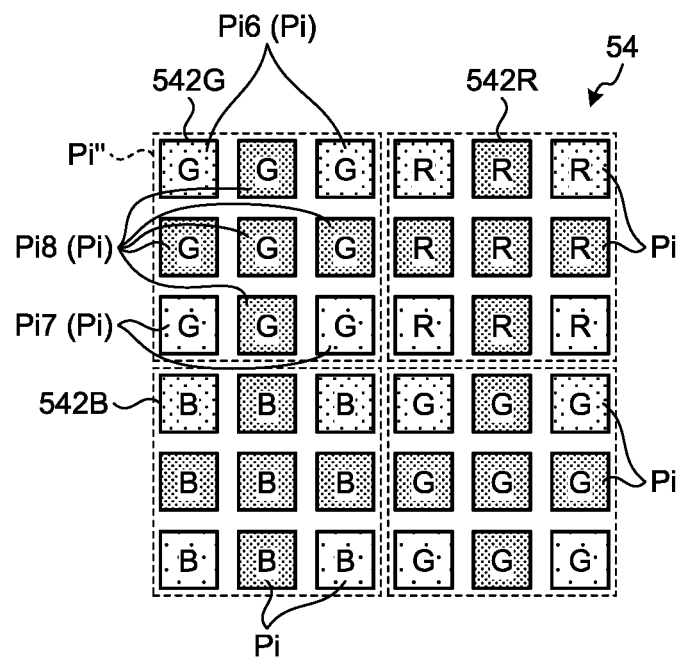
FIG. 15C is a diagram illustrating the first modification of the first to the fifth embodiments.
Figure 15D:
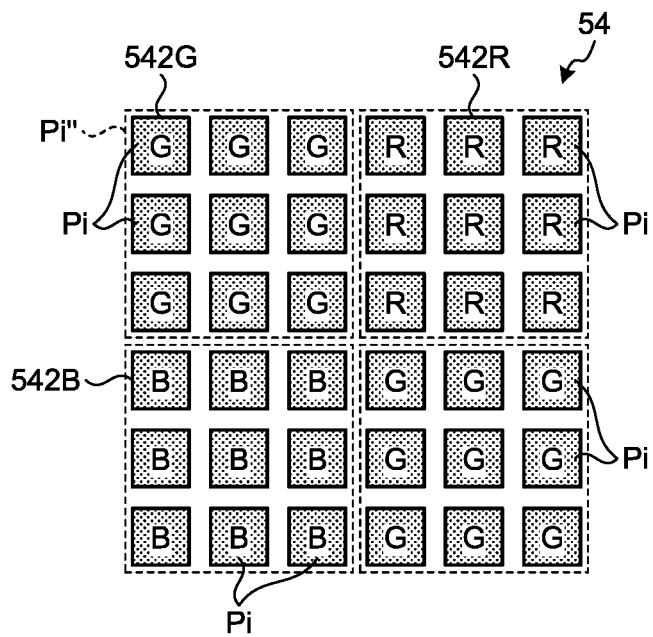
FIG. 15D is a diagram illustrating the first modification of the first to the fifth embodiments.

FIG. 15A to FIG. 15D are diagrams illustrating a first modification of the first to the fifth embodiments. Specifically, FIG. 15A is a diagram for describing the normal mode and corresponding to FIG. 3A. FIG. 15B and FIG. 15C are diagrams for describing the HDR mode and corresponding to FIG. 3B. FIG. 15D is a diagram for describing the high-sensitivity mode and corresponding to FIG. 3C.

In the first to the fifth embodiments described above, all the pixels of the imaging element 541 are sectioned into a plurality of sets, one set consisting of four adjacent pixels Pi; however, the number of pixels Pi included in one set is not limited to four and may be other number. For example, as presented by dashed lines in FIG. 15A to FIG. 15D, all the pixels of the imaging element 541 are sectioned into a plurality of sets: one set consists of nine adjacent pixels Pi (three pixels Pi in the same row and three pixels Pi in the same column constitute one set of nine pixels Pi). In regard to each of the R filter 542R, the G filter 542G, or the B filter 542B, as illustrated in FIG. 15A to FIG. 15D, the nine pixels Pi included in one set have the same filter, and when the one set (nine pixels Pi) is regarded as one pixel, the filters are disposed in the Bayer array.

Description is now made of the normal mode, the HDR mode, and the high-sensitivity mode in the above structure with reference to FIG. 15A to FIG. 15D. In FIG. 15A to FIG. 15D, the exposure time of each pixel Pi is expressed by the depth of color of each pixel Pi (the exposure time is shorter as the color is lighter) and corresponding to FIG. 3A to FIG. 3C.

In the normal mode, the exposure time of all the pixels of the imaging element 541 is set to be the same (for example, if the frame rate is 60 fps, the exposure time is 1/60 seconds) as illustrated in FIG. 15A. The imaging units 54 and 54A output pixel signals, output from respective pixels Pi, each serving as the pixel signal of one pixel.

In the case of the HDR mode illustrated in FIG. 15B, in all the pixels of the imaging element 541, the exposure time of the three pixels Pi3 on the uppermost side among the nine pixels Pi included in one set in FIG. 15B is set to be the same (for example, if the frame rate is 60 fps, the exposure time is 1/60 seconds). In all the pixels of the imaging element 541, the exposure time of the three pixels Pi4 adjacent to the three pixels Pi3 among the nine pixels Pi included in one set is set to be the same but shorter than the exposure time of the pixels Pi3 (for example, if the frame rate is 60 fps, the exposure time is 1/120 seconds). In addition, in all the pixels of the imaging element 541, the exposure time of the three pixels Pi5 adjacent to the three pixels Pi4 among the nine pixels Pi included in one set is set to be the same but shorter than the exposure time of the pixels Pi4 (for example, if the frame rate is 60 fps, the exposure time is 1/240 seconds). The imaging unit 54 outputs addition pixel signals obtained by adding up the pixel signals of the nine pixels Pi3 to Pi5 included in one set, each serving as the pixel signal of one pixel Pi" (FIG. 15B) for each set.

In the case of the HDR mode illustrated in FIG. 15C, in all the pixels of the imaging element 541, the exposure time of the five pixels Pi8 excluding the pixels Pi6 and Pi7 at the four corners of the nine pixels Pi included in one set is set to be the same (for example, if the frame rate is 60 fps, the exposure time is 1/60 seconds). In all the pixels of the imaging element 541, the exposure time of the pixels Pi6 at the upper corners of the nine pixels Pi included in one set in FIG. 15C is set to be the same but shorter than the exposure time of the pixels Pi8 (for example, if the frame rate is 60 fps, the exposure time is 1/120 seconds). In addition, in all the pixels of the imaging element 541, the exposure time of the pixels Pi7 at the lower corners of the nine pixels Pi included in one set in FIG. 15C is set to be the same but shorter than the exposure time of the pixels Pi6 (for example, if the frame rate is 60 fps, the exposure time is 1/240 seconds). The imaging unit 54 outputs addition pixel signals obtained by adding up the pixel signals of the nine pixels Pi6 to Pi8 included in one set, each serving as the pixel signal of one pixel Pi" (FIG. 15C) for each set.

In the case of the high-sensitivity mode, the exposure time of all the pixels of the imaging element 541 is set to be the same (for example, if the frame rate is 60 fps, the exposure time is 1/60 seconds) as illustrated in FIG. 15D. The imaging unit 54 outputs addition pixel signals obtained by adding up the pixel signals of the nine pixels Pi included in one set, each serving as the pixel signal of one pixel Pi" (FIG. 15D) for each set.

Figure 16:
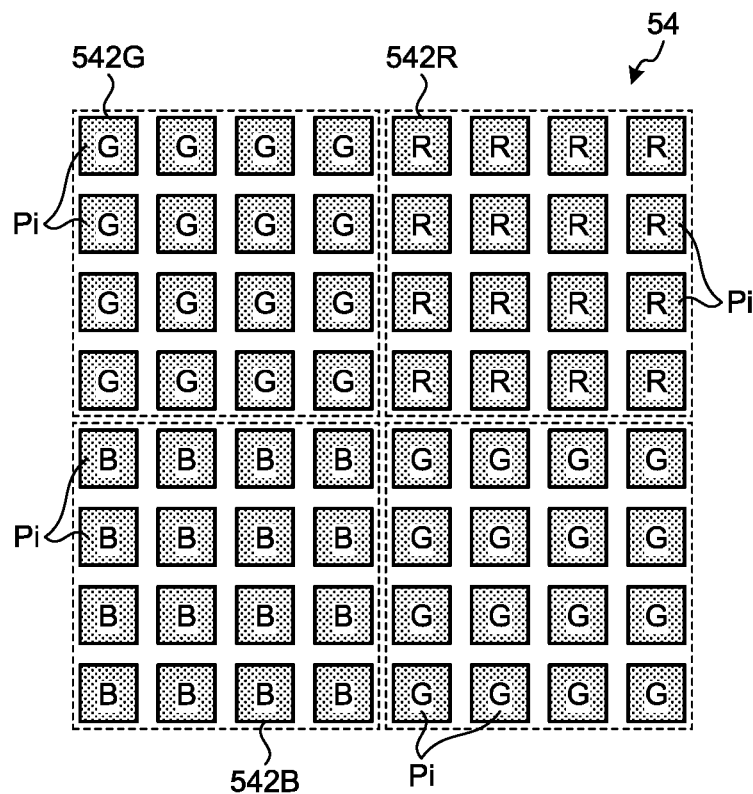
FIG. 16 is a diagram illustrating a second modification of the first to the fifth embodiments.

FIG. 16 is a diagram illustrating a second modification of the first to the fifth embodiments. Specifically, FIG. 16 is a schematic diagram illustrating the arrangement of the pixels Pi of the imaging element 541 and corresponding to FIG. 3A to FIG. 3C.

As indicated by dashed lines in FIG. 16, all the pixels of the imaging element 541 may be sectioned into a plurality of sets: one set consists of 16 adjacent pixels Pi (four pixels Pi in the same row and four pixels Pi in the same column constitute one set of 16 pixels Pi). In regard to each of the R filter 542R, the G filter 542G, or the B filter 542B, as illustrated in FIG. 16, the 16 pixels Pi included in one set have the same filter, and when the one set (16 pixels Pi) is regarded as one pixel, the filters are disposed in the Bayer array.

In the case of the above structure, the exposure time of all the pixels of the imaging element 541 is the same in the normal mode. The imaging units 54 and 54A output pixel signals output from respective pixels Pi, each serving as the pixel signal of one pixel.

In the HDR mode, in all the pixels of the imaging element 541, the exposure time of at least one pixel Pi among the 16 pixels Pi included in one set is set to be different from that of the other pixels Pi. The imaging unit 54 outputs addition pixel signals obtained by adding up the pixel signals of the 16 pixels Pi included in one set, each serving as the pixel signal of one pixel for each set.

Furthermore, in the high-sensitivity mode, the exposure time of all the pixels of the imaging element 541 is set to be the same. The imaging unit 54 outputs addition pixel signals obtained by adding up the pixel signals of the 16 pixels Pi included in one set, each serving as the pixel signal of one pixel for each set.

The arrangement of the R filter 542R, the G filter 542G, and the B filter 542B in the second embodiment described above is not limited to the arrangement illustrated in FIG. 3A, FIG. 15A, or FIG. 16. Instead of sectioning all the pixels of the imaging element 541, the filters may be disposed in the Bayer array so that the pixels Pi adjacent in the row direction or the column direction have different filters.

Figure 17:
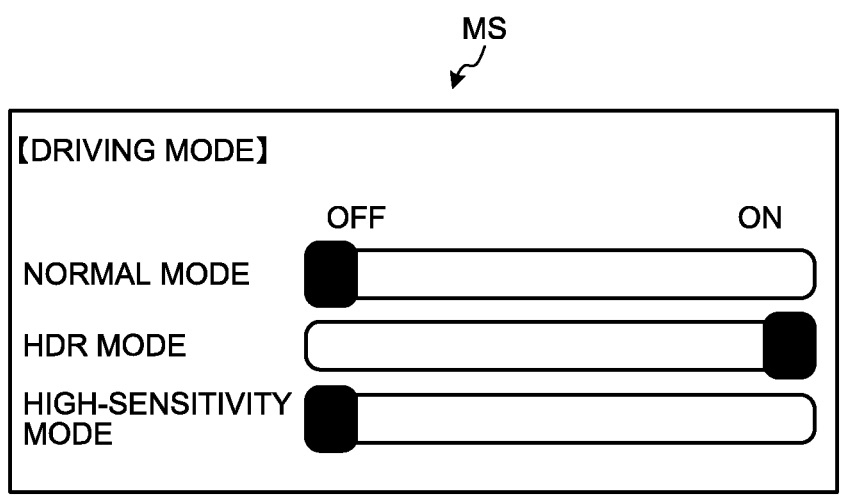
FIG. 17 is a diagram illustrating a third modification of the first to the fifth embodiments.

FIG. 17 is a diagram illustrating a third modification of the first to the fifth embodiments.

In the first and the third to the fifth embodiments described above, the driving mode of the imaging unit 54 is set to any of the normal mode, the HDR mode, and the high-sensitivity mode automatically; however, the mode may be set by the user's input operation or the user's voice. For example, as illustrated in FIG. 17, the user may select any of the normal mode, the HDR mode, and the high-sensitivity mode by operating the input unit 95 or an operation unit (not illustrated) provided to the camera head 5 on a menu screen MS displayed on the display device 7. This similarly applies to the operation mode of the Y gamma-correction unit 9231.

Figure 18:
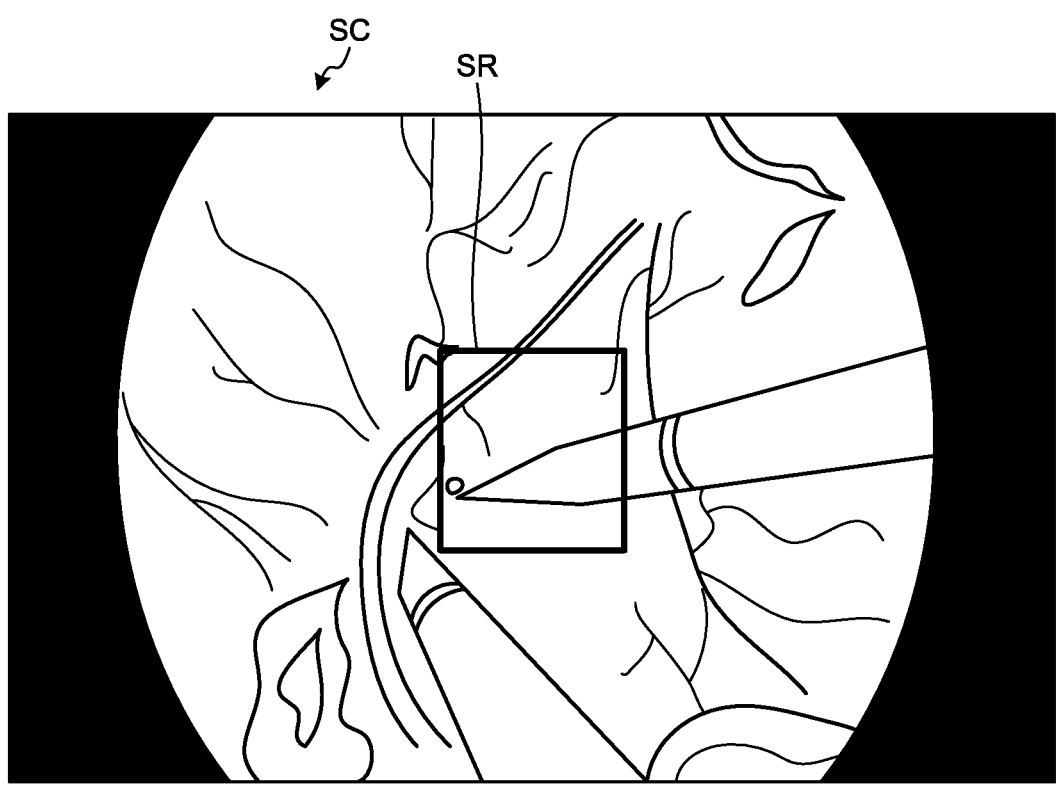
FIG. 18 is a diagram illustrating a fourth modification of the first to the fifth embodiments.

FIG. 18 is a diagram illustrating a fourth modification of the first to the fifth embodiments.

In the first to the fifth embodiments, all the pixels of the imaging element 541 are driven in any driving mode selected from the normal mode, the HDR mode, and the high-sensitivity mode; however, only the pixels in the range selected by the user's input operation or the user's voice may be driven in any of the above driving modes. For example, as illustrated in FIG. 18, only the pixels in a selected range SR selected by the user's operation in the input unit 95 or an operation unit (not illustrated) provided to the camera head 5 on a display screen SC of the display device 7 may be driven in any of the above driving modes. The pixels out of the selected range SR are driven in, for example, the normal mode. The Y gamma-correction unit 9231 performs the Y gamma-correction by the Y gamma-curve set by the mode setting units 941 and 941A, on only the luminance signals (Y signals) corresponding to the pixels in the selected range SR among the luminance signals (Y signals) included in the image signals (Y, $C_B/C_R$ signals) subjected to the RGB process in the RGB processing unit 922.

In the first to the fifth embodiments described above, the histogram of the luminance signal (Y signal) is calculated and based on the histogram, the driving mode of the imaging unit 54 and the operation mode of the Y gamma-correction units 9231 and 9231B are set; however, the setting of the operation mode is not limited to this procedure. For example, the brightness of the entire image obtained by the imaging unit 54 is determined and based on the determination result, the driving mode of the imaging unit 54 and the operation mode of the Y gamma-correction units 9231 and 9231B may be set.

In the first and the third to the fifth embodiments described above, three driving modes of the normal mode, the HDR mode, and the high-sensitivity mode are prepared as the driving mode of the imaging unit 54; however, only two driving modes of these three driving modes may be prepared. In the first to the fifth embodiments described above, the four operation modes of the first to the fourth operation modes are prepared as the operation mode of the Y gamma-correction units 9231 and 9231B; however, the number of operation modes is not limited to the particular number as long as there are two or more operation modes with different Y gamma-curves.

In the first to the fifth embodiments described above, the first to the third thresholds to Th3 may be changeable either manually or automatically. The total number of pixels when the histogram is calculated is different depending on the driving mode of the imaging unit 54 as of this moment. That is to say, the total number of pixels is different when the driving mode is the normal mode, and the HDR mode or the high-sensitivity mode (the total pixels are fewer in the HDR mode and the high-sensitivity mode than in the normal mode). Therefore, for example, the first threshold Th1 may be automatically set lower when the driving mode of the imaging unit 54 as of this moment is the HDR mode or the high-sensitivity mode than when it is the normal mode.

In the first to the fifth embodiments described above, the signal processing units 92 and 92B, the mode setting units 941 and 941A, and the imaging control units 942 and 942A may be provided outside the control devices 9, 9A, and 9B. For example, the signal processing units 92 and 92B, the mode setting units 941 and 941A, and the imaging control units 942 and 942A may be provided to the camera heads 5 and 5A, the connectors CN1 and CN2, the endoscope 11, or the surgical microscope 12.

In the first to the fifth embodiments described above, the light control of the light source device 3 may be performed in accordance with the driving mode of the imaging units 54 and 54A and the operation mode of the Y gamma-correction units 9231 that are set by the mode setting unit 941.

The relation of the exposure time of the pixels included in one set in the HDR mode described in the first and the third to the fifth embodiments and the first and the second modifications described above is not limited to the relation described in the first and the third to the fifth embodiments and the first and the second modifications. It is only necessary that the exposure time of at least one pixel of all the pixels included in one set is different from that of the other pixels. Therefore, for example, the exposure time of all the pixels may be different.

In the third to the fifth embodiments, the imaging unit 54 may be driven only in the normal mode, which is similar to the second embodiment.

The medical signal processing device according to the present disclosure includes the Y gamma-correction unit that performs the Y gamma-correction on the luminance signal for each pixel in the image obtained by the imaging unit.

Therefore, in the case of displaying an image not suitable for observation (for example, an image where a bright part results in white, an image where a dark part results in black, or an image where a forceps or white gauze gets in the image of a subject to make the image appear brighter as a whole), the Y gamma-correction is performed. That is to say, when the pixel has a low luminance value, the luminance value may be increased by the Y gamma-correction, and when the pixel has a high luminance value, the luminance value may be decreased by the Y gamma-correction. By the Y gamma-correction, an image suitable for observation may be displayed and the convenience may be improved.

Therefore, the medical signal processing device according to the present disclosure does not need to have a plurality of imaging elements with different sensitivities, and thus, the effect of improving the convenience without complicating the structure may be obtained.

Moreover, the medical observation system according to the present disclosure includes the aforementioned medical signal processing device, so that the operation and effects similar to those of the aforementioned medical signal processing device may be obtained.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical signal processing device, comprising:
   circuitry configured to
      process an image obtained by an image sensor including a plurality of pixels,
      generate a video signal for display,
      set an operation mode of the Y gamma-correction to any of a first, second, or third operation mode on the basis of brightness of the image obtained by the imaging sensor, wherein a Y gamma-curve in the Y gamma-correction is different in each of the operation modes,
      calculate a histogram of the luminance signal for the image obtained by the imaging sensor, wherein luminance values in the histogram are grouped into a dark area comprising luminance values below a first threshold, an intermediate area comprising luminance values between the first threshold and a second threshold, and a bright area comprising luminance values above the second threshold,
      set the operation mode of the Y gamma-correction to the first operation mode in response to a determination that the calculated histogram is a histogram of a first pattern having peaks in both the dark area and the bright area,
      set the operation mode of the Y gamma-correction to the second operation mode in response to a determination that the calculated histogram is a histogram of a second pattern having a peak only in the dark area,
      set the operation of the Y gamma-correction to the third operation mode in response to a determination that the calculated histogram is a histogram of a third pattern having a peak only in the bright area, and
      perform the Y gamma-correction on a luminance signal for each pixel in the image obtained by the imaging sensor, wherein
   the imaging sensor images a subject image taken in by an endoscope inserted into a subject,
   the image obtained by the imaging sensor includes the subject image and a mask area other than the subject image,
   the circuitry is further configured to detect border points between the subject image and the mask area on the basis of the luminance signal for each pixel in the image obtained by the imaging sensor, and
   the Y gamma-correction is performed only on an area surrounded by the detected border points in the entire image obtained by the imaging sensor.

2. A medical observation system comprising:
   an imaging sensor including a plurality of pixels;
   a medical signal processing device including circuitry configured to process the image obtained by the image sensor and generate a video signal for display;
   a display device that displays an image based on the video signal for display generated by the medical signal processing device, wherein
   the circuitry is further configured to set an operation mode of the Y gamma-correction to any of a first, second, or third operation mode on the basis of brightness of the image obtained by the imaging sensor, wherein a Y gamma-curve in the Y gamma-correction is different in each of the operation modes, and
   the circuitry is further configured to
      calculate a histogram of the luminance signal for the image obtained by the imaging sensor, wherein luminance values in the histogram are grouped into a dark area comprising luminance values below a first threshold, an intermediate area comprising luminance values between the first threshold and a second threshold, and a bright area comprising luminance values above the second threshold,
      set the operation mode of the Y gamma-correction to the first operation mode in response to a determination that the calculated histogram is a histogram of a first pattern having peaks in both the dark area and the bright area,
      set the operation mode of the Y gamma-correction to the second operation mode in response to a determination that the calculated histogram is a histogram of a second pattern having a peak only in the dark area,
      set the operation of the Y gamma-correction to the third operation mode in response to a determination that the calculated histogram is a histogram of a third pattern having a peak only in the bright area, and
      perform the Y gamma-correction on a luminance signal for each pixel in the image obtained by the imaging sensor, wherein
   the imaging sensor images a subject image taken in by an endoscope inserted into a subject,
   the image obtained by the imaging sensor includes the subject image and a mask area other than the subject image,
   the circuitry is further configured to detect border points between the subject image and the mask area on the basis of the luminance signal for each pixel in the image obtained by the imaging sensor, and
   the Y gamma-correction is performed only on an area surrounded by the detected border points in the entire image obtained by the imaging sensor.

3. The medical signal processing device according to claim 1, wherein the circuitry is further configured to receive an RGB signal representing the image and to convert the RGB signal into luminance and color difference signals.

4. The medical observation system according to claim 2, wherein the circuitry is further configured to receive an RGB signal representing the image and to convert the RGB signal into luminance and color difference signals.

5. The medical observation system according to claim 4, wherein the luminance and color difference signals include Cb/Cr signals.

6. The medical signal processing device according to claim 3, wherein the luminance and color difference signals include Cb/Cr signals.

7. The medical signal processing device according to claim 1, wherein the Y gamma-correction includes one of:
   increasing the luminance value for the pixels for which the luminance value is in the dark area and reducing the luminance value for the pixels for which the luminance value is in the bright area in response to a determination that the calculated histogram is the histogram of the first pattern;

increasing the luminance value for the pixels for which the luminance value is in the dark area and not correcting the luminance value for the pixels for which the luminance value is in the bright area in response to a determination that the calculated histogram is the histogram of the second pattern; or not correcting the luminance value for the pixels for which the luminance value is in the dark area and decreasing the luminance value for the pixels for which the luminance value is in the bright area in response to a determination that the calculated histogram is the histogram of the third pattern.

* * * * *